US006632826B1

(12) United States Patent
Demont et al.

(10) Patent No.: US 6,632,826 B1
(45) Date of Patent: Oct. 14, 2003

(54) CARBOCYCLIC HIV PROTEASE INHIBITORS

(75) Inventors: Emmanuel Demont, Welwyn Garden (GB); Joseph Armstrong Martin, Harpenden (GB); Sally Redshaw, Hitchin (GB); Steven Swallow, Los Altos, CA (US)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 10/253,561

(22) Filed: Sep. 24, 2002

(30) Foreign Application Priority Data

Sep. 28, 2001 (GB) ............................................. 0123467

(51) Int. Cl.[7] ........................ A61K 31/18; A61K 31/47; C07C 311/05; C07C 215/36
(52) U.S. Cl. ........................ 514/311; 514/605; 546/172; 564/99
(58) Field of Search ................................ 514/311, 605; 546/172; 564/99

(56) References Cited

FOREIGN PATENT DOCUMENTS

| EP | 512 343 | 11/1992 |
|----|---------|---------|
| EP | 604 184 | 6/1994 |
| EP | 604 185 | 6/1994 |
| WO | WO 95/20962 | 8/1995 |

OTHER PUBLICATIONS

Munroe et al., Bioorganice & Medicinal Chemistry Letter, 5, pp. 2897–2902 (1995).
Thomas et al., Bioorganic & Medicinal Chemistry Letter, 4, pp. 2759–2762 (1994).
Jungheim et al., J. Med. Chem., 39, pp. 96–108 (1996).
Matayoshi et al., Science, 247, pp. 954–958 (1990).

*Primary Examiner*—Peter O'Sullivan
(74) *Attorney, Agent, or Firm*—George W. Johnston; Dennis P. Tramaloni; Lyman H. Smith

(57) ABSTRACT

The present invention is concerned with novel HIV protease Inhibitors of formula I

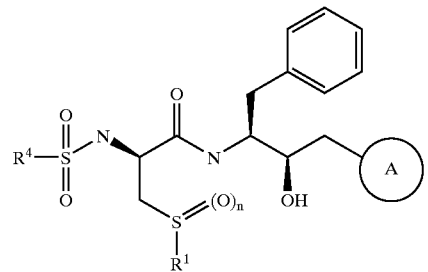

as individual isomers, racemates, non-racemic mixtures or mixtures of diastereoisomers; wherein n, $R^1$ and $R^4$ are as described herein. The compounds of formula I are peptide mimetics which act as inhibitors of the HIV aspartyl protease, an essential enzyme in the replicative life cycle of HIV.

8 Claims, No Drawings

CARBOCYCLIC HIV PROTEASE INHIBITORS

BACKGROUND OF THE INVENTION

This invention is concerned with novel HIV protease inhibitors, a process for their manufacture, pharmaceutical compositions and the use of such compounds in medicine. In particular, the compounds are peptide mimetics which act as inhibitors of the HIV aspartyl protease, an essential enzyme in the replicative life cycle of HIV. Consequently, the compounds of this invention may be advantageously used in the treatment of HIV infection, either alone or in combination with other inhibitors of HIV viral replication or with pharmacoenhancers such as cytochrome P450 inhibitors.

The human immunodeficiency virus HIV is the causative agent of acquired immunodeficiency syndrome (AIDS), a disease characterised by the destruction of the immune system, particularly of the CD4+ T-cell, with attendant susceptibility to opportunistic infections. HIV infection is also associated with a precursor AIDs-related complex (ARC), a syndrome characterised by symptoms such as persistent generalised lymphadenopathy, fever and weight loss.

In common with other retroviruses, the HIV genome encodes protein precursors known as gag and gag-pol which are processed by the viral protease to afford the protease, reverse transcriptase (RT), endonuclease/integrase and mature structural proteins of the virus core. Interruption of this processing prevents the production of normally infectious virus. Considerable efforts have been directed towards the control of HIV by inhibition of virally encoded enzymes. In particular, much effort has been directed towards the inhibition of HIV protease, and the HIV protease inhibitors (PIs) saquinavir, ritonavir, nelfinavir, indinavir, amprenavir and lopinavir have been approved for treatment of HIV infections. Because of the emergence of resistant virus during monotherapy, current clinical practice is to use such protease inhibitors in combination therapy, typically with RT inhibitors.

The emergence of resistant virus can be attributed to errors introduced by the HIV reverse transcriptase, in conjunction with a high virus replication rate. It is likely that mutations that lead to resistant virus occur spontaneously but remain undetectable until initiation of therapy leads to a selective pressure for the emergence of virus with replicative advantage over the wildtype population. In the context of HIV protease inhibition, accumulation of mutations that lead to a reduction in inhibitor binding while maintaining sufficient substrate turnover can lead to drug resistance. Although the onset of drug resistance can be delayed to some extent by the use of combinations of drugs, there remains a need for more effective HIV protease inhibitors that retain activity against PI-resistant and multi-PI resistant viruses.

SUMMARY OF THE INVENTION

In one aspect of the present invention, there are provided novel compounds which are potent inhibitors of the HIV aspartyl protease and which accordingly show a potential to be efficacious in the treatment of HIV related diseases. Compounds of the invention may also therefore show the potential to inhibit the replication of virus that is resistant to commonly used protease inhibitors.

The compounds of the present invention may be characterized by the following formula I

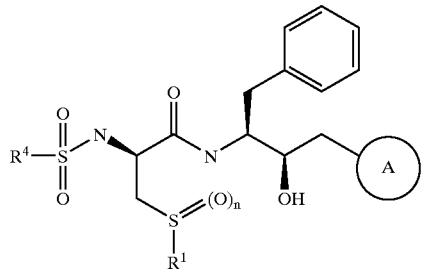

I as individual isomers, racemates, non-racemic mixtures or mixtures of diastereoisomers; wherein n, $R^1$ and $R^4$ are as described below.

The present invention is also directed to pharmaceutical compositions containing compounds of formula I and the use of the compounds of formula I in the treatment or therapy of HIV mediated diseases.

DETAILED DESCRIPTION OF THE INVENTION

The present invention is directed to, inter alia, a compound of formula I,

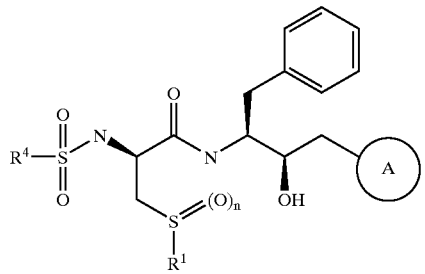

I wherein n is 0, 1 or 2;

$R^1$ is naphthyl, quinolinyl or phenyl, optionally substituted by halogen;

$R^4$ is $(C_1-C_7)$-alkyl;

A is a group

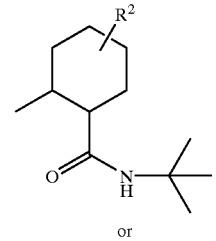

A1 or

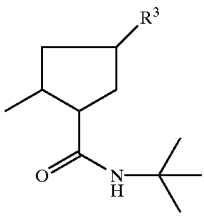

wherein
R² is hydrogen or (C₁–C₇) lower alkoxy; and
R³ is (C₁–C₇)-alkyl;
or pharmaceutically acceptable salts thereof.

The term (C₁–C₇)-alkyl defines an optionally substituted straight or branched alkyl chain carrying 1 to 7 carbon atoms, preferably 1 to 4 carbon atoms. Alkyl preferably stands for methyl, ethyl, n-propyl, i-propyl, n-butyl, i-butyl and t-butyl.

The term (C₁–C₇)-alkoxy defines an optionally substituted straight or branched alkoxy chain carrying 1 to 7 carbon atoms, preferably 1 to 4 carbon atoms. Alkoxy preferably stands for methoxy, ethoxy, n-propoxy, i-propoxy, n-butoxy, i-butoxy and t-butoxy.

The term halogen stands for fluorine, chlorine, bromine and iodine.

The term "racemate" defines a mixture of 50:50 of pure dextrorotatory and levorotatory enantiomers. The term "non racemic" defines mixtures containing pure dextrorotatory and levorotatory enantiomer at ratios different from 50:50 and varying between 1:99 and 99:1.

Compounds of formula (I) which are acidic can form pharmaceutically acceptable salts with bases such as alkali metal hydroxides, e.g. sodium hydroxide, potassium hydroxide and the like; alkaline earth metal hydroxides, e.g. calcium hydroxide, barium hydroxide, magnesium hydroxide and the like; with organic bases e.g. N-ethyl piperidine, dibenzylamine and the like. Those compounds of formula (I) which are basic can form pharmaceutically acceptable salts with inorganic acids, e.g. hydrohalic acids such as hydrochloric acid and hydrobromic acid, sulphuric acid, nitric acid, phosphoric acid and the like; and with organic acids, e.g. acetic acid, tartaric acid, succinic acid, fumaric acid, maleic acid, malic acid, salicylic acid, citric acid, methanesulphonic acid, p-toluene sulphonic acid and the like. The formation and isolation of such salts can be carried out according to methods known in the art.

Preferred compounds of formula I include the following cyclopentanecarboxylic acid tert-butylamides:

2-{2-Hydroxy-3-[2-methanesulfonylamino-3-(naphthalen-2-ylsulfanyl)-propionylamino]-4-phenyl-butyl}-4-methyl-cyclopentanecarboxylic acid tert-butylamide;

2-{2-Hydroxy-3-[2-methanesulfonylamino-3-(quinolin-8-ylsulfanyl)-propionylamino]-4-phenyl-butyl}-4-methyl-cyclopentanecarboxylic acid tert-butylamide;

2-{2-Hydroxy-3-[2-methanesulfonylamino-3-(naphthalen-2-ylsulfanyl)-propionylamino]-4-phenyl-butyl}-4-methyl-cyclopentanecarboxylic acid tert-butylamide;

2-{3-[3-(4-Fluoro-phenylsulfanyl)-2-methanesulfonylamino-propionylamino]-2-hydroxy-4-phenyl-butyl}-4-methyl-cyclopentanecarboxylic acid tert-butylamide;

2-{3-[3-(4-Fluoro-phenylsulfanyl)-2-methanesulfonylamino-propionylamino]-2-hydroxy-4-phenyl-butyl}-4-methyl-cyclopentanecarboxylic acid tert-butylamide;

2-{2-Hydroxy-3-[2-methanesulfonylamino-3-(naphthalene-2-sulfinyl)-propionylamino]-4-phenyl-butyl}-4-methyl-cyclopentanecarboxylic acid tert-butylamide;

2-{2-Hydroxy-3-[2-methanesulfonylamino-3-(naphthalene-2-sulfonyl)-propionylamino]-4-phenyl-butyl}-4-methyl-cyclopentanecarboxylic acid tert-butylamide;

2-{2-Hydroxy-3-[2-methanesulfonylamino-3-(naphthalene-2-sulfonyl)-propionylamino]-4-phenyl-butyl}-4-methyl-cyclopentanecarboxylic acid tert-butylamide;

2-{2-Hydroxy-3-[2-methanesulfonylamino-3-(quinoline-8-sulfonyl)-propionylamino]-4-phenyl-butyl}-4-methyl-cyclopentanecarboxylic acid tert-butylamide;

2-{3-[3-(4-Fluoro-benzenesulfonyl)-2-methanesulfonylamino-propionylamino]-2-hydroxy-4-phenyl-butyl}-4-methyl-cyclopentanecarboxylic acid tert-butylamide.

Further preferred compounds of formula I include the following cyclohexanecarboxylic acid tert-butylamides:

2-{2-Hydroxy-3-[2-methanesulfonylamino-3-(naphthalen-1-ylsulfanyl)-propionylamino]-4-phenyl-butyl}-4-methoxy-cyclohexanecarboxylic acid tert-butylamide;

N-tert-Butyl-2-[2-hydroxy-3-[[N2-(methanesulfonyl)-S-(2-naphthyl)-D-cysteinyl]amino]-4-phenylbutyl]-4-methoxy-1-cyclohexanecarboxamide;

2-{3-[3-(4-Fluoro-phenylsulfanyl)-2-methanesulfonylamino-propionylamino]-2-hydroxy-4-phenyl-butyl}-4-methoxy-cyclohexanecarboxylic acid tert-butylamide;

2-{2-Hydroxy-3-[2-methanesulfonylamino-3-(naphthalen-1-ylsulfanyl)-propionylamino]-4-phenyl-butyl}-5-methoxy-cyclohexanecarboxylic acid tert-butylamide;

2-{2-Hydroxy-3-[2-methanesulfonylamino-3-(naphthalen-2-ylsulfanyl)-propionylamino]-4-phenyl-butyl}-5-methoxy-cyclohexanecarboxylic acid tert-butylamide;

2-{2-Hydroxy-3-[2-methanesulfonylamino-3-(quinolin-8-ylsulfanyl)-propionylamino]-4-phenyl-butyl}-5-methoxy-cyclohexanecarboxyl acid tert-butylamide;

2-{3-[3-(4-Fluoro-phenylsulfanyl)-2-methanesulfonylamino-propionylamino]-2-hydroxy-4-phenyl-butyl}-5-methoxy-cyclohexanecarboxylic acid tert-butylamide;

2-{2-Hydroxy-3-[2-methanesulfonylamino-3-(naphthalen-1-ylsulfanyl)-propionylamino]-4-phenyl-butyl}-cyclohexanecarboxylic acid tert-butylamide;

2-{2-Hydroxy-3-[2-methanesulfonylamino-3-(naphthalen-1-ylsulfinyl)-propionylamino]-4-phenyl-butyl}-4-methoxy-cyclohexanecarboxylic acid tert-butylamide;

2-{2-Hydroxy-3-[2-methanesulfonylamino-3-(naphthalene-2-sulfinyl)-propionylamino]-4-phenyl-butyl}-4-methoxy-cyclohexanecarboxylic acid tert-butylamide;

2-{3-[3-(4-Fluoro-benzenesulfinyl)-2-methanesulfonylamino-propionylamino]-2-hydroxy-4-phenyl-butyl}-4-methoxy-cyclohexanecarboxylic acid tert-butylamide;

2-{2-Hydroxy-3-[2-methanesulfonylamino-3-(naphthalene-1-sulfinyl)-propionylamino]-4-phenyl-butyl}-5-methoxy-cyclohexanecarboxylic acid tert-butylamide;

2-{2-Hydroxy-3-[2-methanesulfonylamino-3-(naphthalene-2-sulfinyl)-propionylamino]-4-phenyl-butyl-5-methoxy-cyclohexanecarboxylic acid tert-butylamide;

2-{2-Hydroxy-3-[2-methanesulfonylamino-3-(naphthalene-1-sulfinyl)-propionylamino]-4-phenyl-butyl}-cyclohexanecarboxylic acid tert-butylamide;

2-{2-Hydroxy-3-[2-methanesulfonylamino-3-(naphthalene-1-sulfonyl)-propionylamino]-4-phenyl-butyl}-4-methoxy-cyclohexanecarboxylic acid tert-butylamide;

N-tert-Butyl-2-[2-hydroxy-3-[[N2-(methanesulfonyl)-S-(2-naphthyl)-D-cysteinyl]amino]-4-phenylbutyl]-4-methoxy-1-cyclohexanecarboxamide S,S-dioxide;

2-{3-[3-(4-Fluoro-benzenesulfonyl)-2-methanesulfonylamino-propionylamino-]2-hydroxy-4-phenyl-butyl}-4-methoxy-cyclohexanecarboxylic acid tert-butylamide;

2-{2-Hydroxy-3-[2-methanesulfonylamino-3-(naphthalene-1-sulfonyl)-propionylamino]-4-phenyl-butyl}-5-methoxy-cyclohexanecarboxylic acid tert-butylamide;

2-{2-Hydroxy-3-[2-methanesulfonylamino-3-(naphthalene-2-sulfonyl)-propionylamino]-4-phenyl-butyl}-5-methoxy-cyclohexanecarboxylic acid tert-butylamide;

2-{2-Hydroxy-3-[2-methanesulfonylamino-3-(quinoline-8-sulfonyl)-propionylamino]-4-phenyl-butyl}-5-methoxy-cyclohexanecarboxylic acid tert-butylamide;

2-{3-[3-(4-Fluoro-benzenesulfonyl)-2-methanesulfonylamino-propionylaminol]-2-hydroxy-4-phenyl-butyl}-5-methoxy-cyclohexanecarboxylic acid tert-butylamide;

2-{2-Hydroxy-3-[2-methanesulfonylamino-3-(naphthalene-1-sulfonyl)-propionylamino]-4-phenyl-butyl}-cyclohexanecarboxylic acid tert-butylamide;

2-{2-Hydroxy-3-[2-methanesulfonylamino-3-(quinoline-8-sulfonyl)-propionylamino]-4-phenyl-butyl}-4-methoxy-cyclohexanecarboxylic acid tert-butylamide;

2-{2-Hydroxy-3-[2-methanesulfonylamino-3-(quinoline-2-sulfonyl)-propionylamino]-4-phenyl-butyl}-4-methoxy-cyclohexanecarboxylic acid tert-butylamide.

Preferred compounds of the invention are compounds of formula 1 wherein
n is 1 or 2
$R^1$ is naphthyl, quinolinyl or phenyl
$R^4$ is methyl
A is a group A1 or A2 wherein
  $R^2$ is hydrogen or methoxy
  $R^3$ is $(C_1-C_4)$-alkyl.

Further preferred compounds of the invention are compounds of formula 1 wherein
n is 1 or 2
$R^1$ is naphthyl,
$R^4$ is methyl
A is a group A1 or A2 wherein
  $R^2$ is hydrogen or methoxy
  $R^3$ is $(C_1-C_4)$-alkyl.

Still further preferred compounds of the invention are compounds of formula 1 wherein n is 2
$R^1$ is naphthyl,
$R^4$ is methyl
A is a group A1 or A2 wherein
  $R^2$ is methoxy
  $R^3$ is methyl.

The compounds provided by the present invention, or prodrugs thereof, are potent inhibitors of the HIV aspartyl protease, an essential enzyme in the replicative cycle of the HIV virus. They accordingly are therapeutically active substances in the treatment of HIV-mediated diseases and therefore can be used as medicaments, either alone or combined with other therapeutically active agents.

The compounds provided by the present invention are, in particular, useful in combating HIV disease states such as AIDS.

Any functional (i.e. reactive) group present in a side-chain may be protected, with the protecting group being a group which is known per se, for example, as described in "Protective Groups in Organic Synthesis", $2^{nd}$ Ed., T. W. Greene and P. G. M. Wuts, John Wiley & Sons, New York, N.Y., 1991. For example, an amino group can be protected by a tert-butoxycarbonyl (BOC), formyl, trityl, benzyloxycarbonyl (Z or Cbz), 9-fluorenylmethyloxcarbonyl (FMOC), trifluoroacetyl, 2-(biphenylyl)isopropoxycarbonyl or isobornyloxycarbonyl group or in the form of a phthalimido group; or a hydroxyl group can be protected by a tert-butyldimethylsilyl, tetrahydropyranyl, 4-methoxybenzyl, or benzyl or acetate etc.; or a carboxyl group can be protected in the form of an ester, for example as a methyl or benzyl or tert-butyl ester. The protecting group may be retained in the final compound or optionally removed by techniques known in the art.

The compounds of general formula I and their pharmaceutically acceptable salts can be manufactured according to the routes depicted in the following schemes. The intermediates, as well as the final compounds falling within the scope of the present invention, may be obtained as mixtures of enantiomers and/or diastereomers which have not been separated further.

While the group BOC is used here below for elucidating the reaction pathways, any other suitable amino protecting group (e.g. those listed above) can be alternatively used.

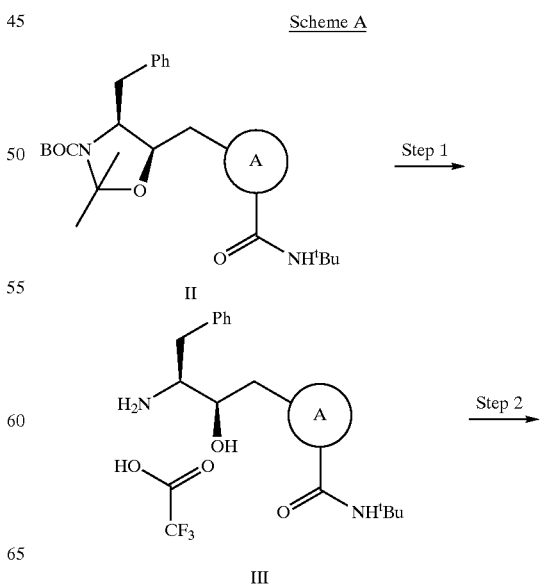

-continued

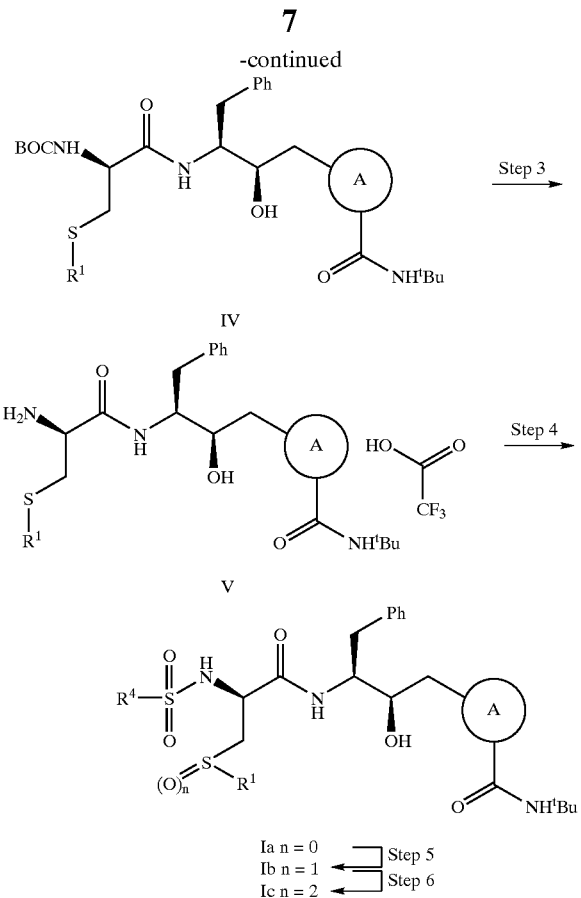

Ia n = 0 ⟵ Step 5
Ib n = 1 ⟵ Step 6
Ic n = 2

Step 1: trifluoroacetic acid water, dichloromethane, 0° C. to room temperature.
Step 2: BOC-amino acid, 1-(3-dimethylaminopropyl)-3-ethylcarbodiimide hydrochloride, 1-hydroxybenzotriazole, N-ethyl morpholine, 4-(dimethylamino)pyridine, dichloromethane,N,N-dimethylform amide, 0° C. to room temperature.
Step 3: trifluoroacetic acid, water dichloromethane, 0° C. to room temperature.
Step 4: C1–C7-alkanesulfonic anhydride or methanesulfonic chloride, N -ethyl morpholine, dichloromethane, 0° C. to room temperature.
Step 5: meta-chloroperbenzoic acid, dichloromethane, -10° C.
Step 6: meta-chloroperbenzoic acid, dichloromethane, room temperature.

According to scheme A, a compound of general formula Ia, b or c can be obtained from a compound of general formula II. Compound II can be deprotected in the presence of a strong acid such as trifluoroacetic acid in e.g. tetrahydrofuran or dichloromethane, after addition of water, and at a temperature varying between 0° C. and room temperature (r.t., 25° C.). Other suitable strong acids are hydrogen chloride in e.g. water, ethyl acetate or diethylether.

The amine of general formula III thus obtained can be coupled with the appropriate BOC-protected D-amino acid (the synthesis of which is depicted in scheme I) after activating the latter by any conventional method employed to generate peptide bonds. This includes for example the formation of the corresponding hydroxybenzotriazole ester in the presence of a non-nucleophilic base such as triethylamine, pyridine or N-ethyl morpholine.

This reaction can be carried out in a solvent such as tetrahydrofuran or dichloromethane, optionally in the presence of a catalytic quantity of 4-(dimethylamino)pyridine. For solubilisation purposes, the reaction may take place at a temperature between –20° C. and 50° C. and, more preferably, between 0° C. and room temperature.

The removal of the BOC protecting group from the intermediate of general formula IV may take place according to the same procedure applied for deprotecting the compound of general formula II. The corresponding sulphonamide of general formula Ia can be then obtained by reacting the amine of formula V with a sulfonic anhydride or sulfonyl chloride according to methods described in the art, for example by reacting methanesulfonic anhydride (or methanesulphonyl chloride) in a solvent such as tetrahydrofuran, pyridine or dichloromethane, and at a temperature ranging from –40° C. to 100° C., preferably from 0° C. to room temperature in the presence of an organic base such as N-ethyl morpholine.

The compound of general formula Ia can be oxidised to the corresponding sulfoxide of formula Ib or to the corresponding sulfone of general formula Ic, by treatment with an oxidising agent (e.g. metachloroperbenzoic acid) in an organic solvent such as dichloromethane, tetrahydrofuran or methanol, and at a temperature ranging from –20° C. to 50° C., preferably from 0° C. to room temperature.

The compound of general formula IIi, that is the compound of general formula II Wherein the core of A is a 4-methylcyclopentane, can be obtained from compound VIi according to scheme B.

Scheme B

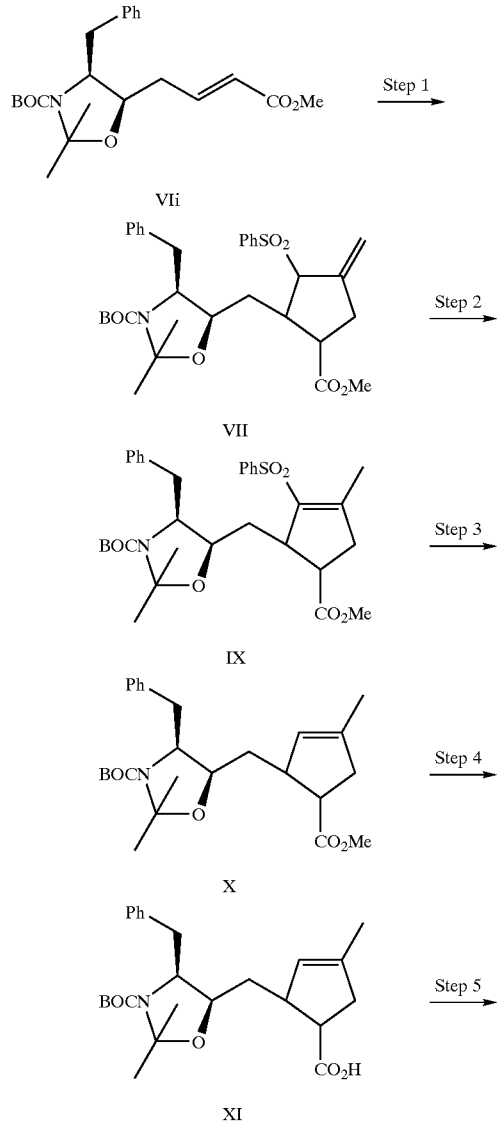

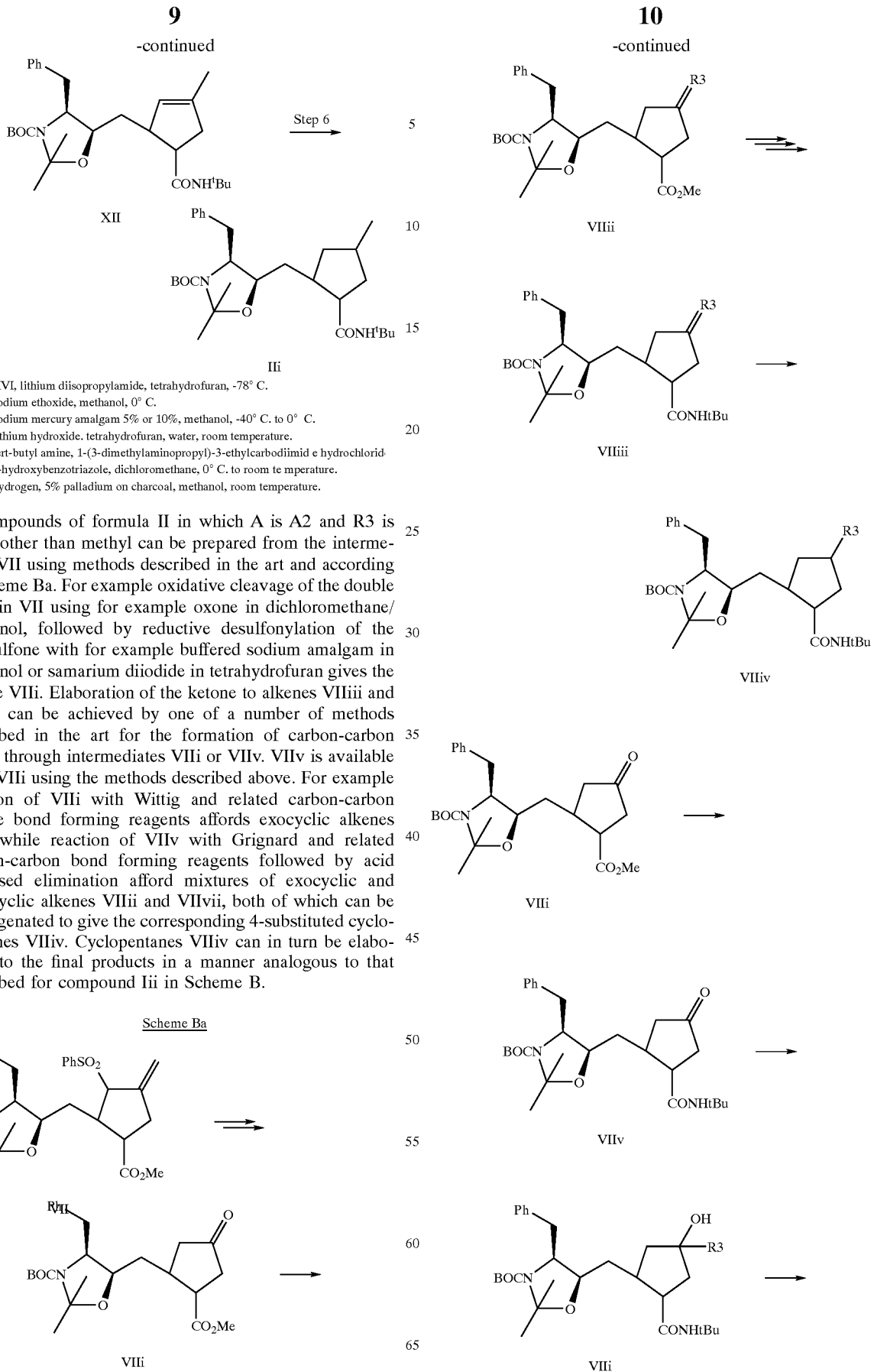

Step 1: XVI, lithium diisopropylamide, tetrahydrofuran, -78° C.
Step 2: sodium ethoxide, methanol, 0° C.
Step 3: sodium mercury amalgam 5% or 10%, methanol, -40° C. to 0° C.
Step 4: lithium hydroxide. tetrahydrofuran, water, room temperature.
Step 5: tert-butyl amine, 1-(3-dimethylaminopropyl)-3-ethylcarbodiimid e hydrochlorid 1-hydroxybenzotriazole, dichloromethane, 0° C. to room te mperature.
Step 6: hydrogen, 5% palladium on charcoal, methanol, room temperature.

Compounds of formula II in which A is A2 and R3 is C1–7 other than methyl can be prepared from the intermediate VII using methods described in the art and according to scheme Ba. For example oxidative cleavage of the double bond in VII using for example oxone in dichloromethane/methanol, followed by reductive desulfonylation of the ketosulfone with for example buffered sodium amalgam in methanol or samarium diiodide in tetrahydrofuran gives the ketone VIIi. Elaboration of the ketone to alkenes VIIiii and VIIvii can be achieved by one of a number of methods described in the art for the formation of carbon-carbon bonds through intermediates VIIi or VIIv. VIIv is available from VIIi using the methods described above. For example reaction of VIIi with Wittig and related carbon-carbon double bond forming reagents affords exocyclic alkenes VIIi, while reaction of VIIv with Grignard and related carbon-carbon bond forming reagents followed by acid catalysed elimination afford mixtures of exocyclic and endocyclic alkenes VIIii and VIIvii, both of which can be hydrogenated to give the corresponding 4-substituted cyclopentanes VIIiv. Cyclopentanes VIIiv can in turn be elaborated to the final products in a manner analogous to that described for compound Iii in Scheme B.

-continued

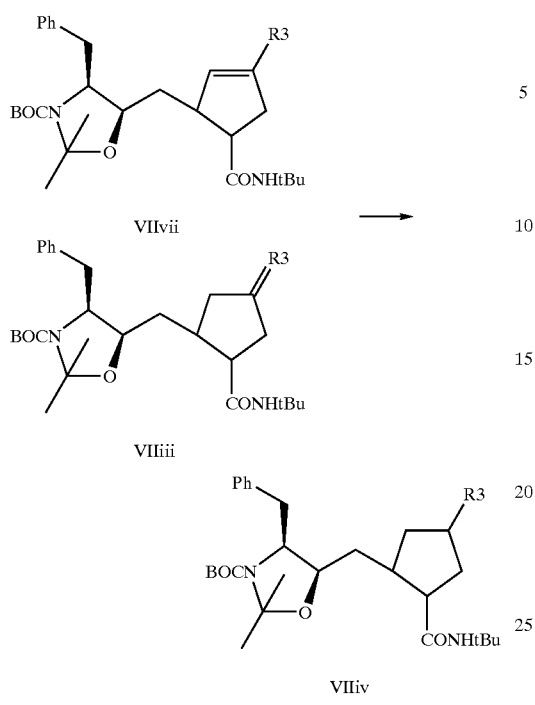

The synthesis of sulfone XVI used for the synthesis of adducts VII is described in scheme C.

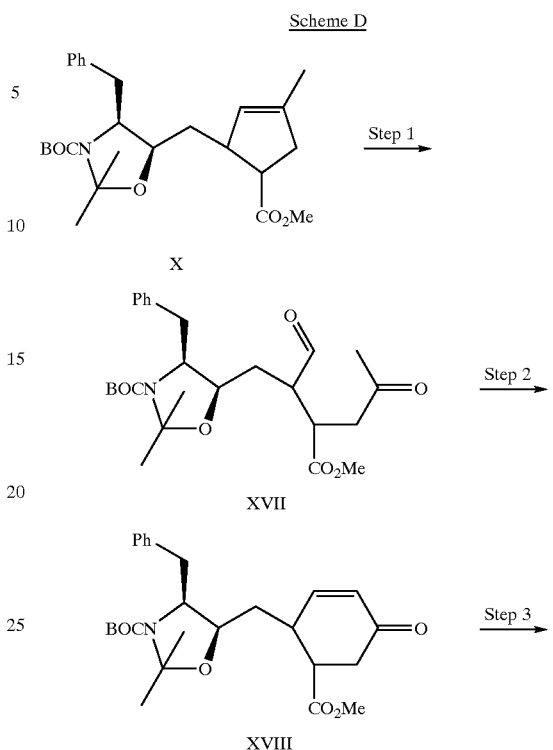

Step 1: 3-chloro-2-methy'1-1propene, benzenesulfinic acid soidium salt, methanol, reflux.
Step 2: methallyl sulfone, sulfuryl chloride, dichloromethane, room temperature to reflux.
Step 3: (2-chloromethyl-prop-2-ene-1-sulfonyl)-benzene, sodium bromide, N,N-dimethylformamide, dibromethane, 100° C.

Compound IIii, that is the compound of general formula II wherein the core of A is a 5-methoxycyclohexyl group, can be obtained according to the route described in scheme D, starting from compound X.

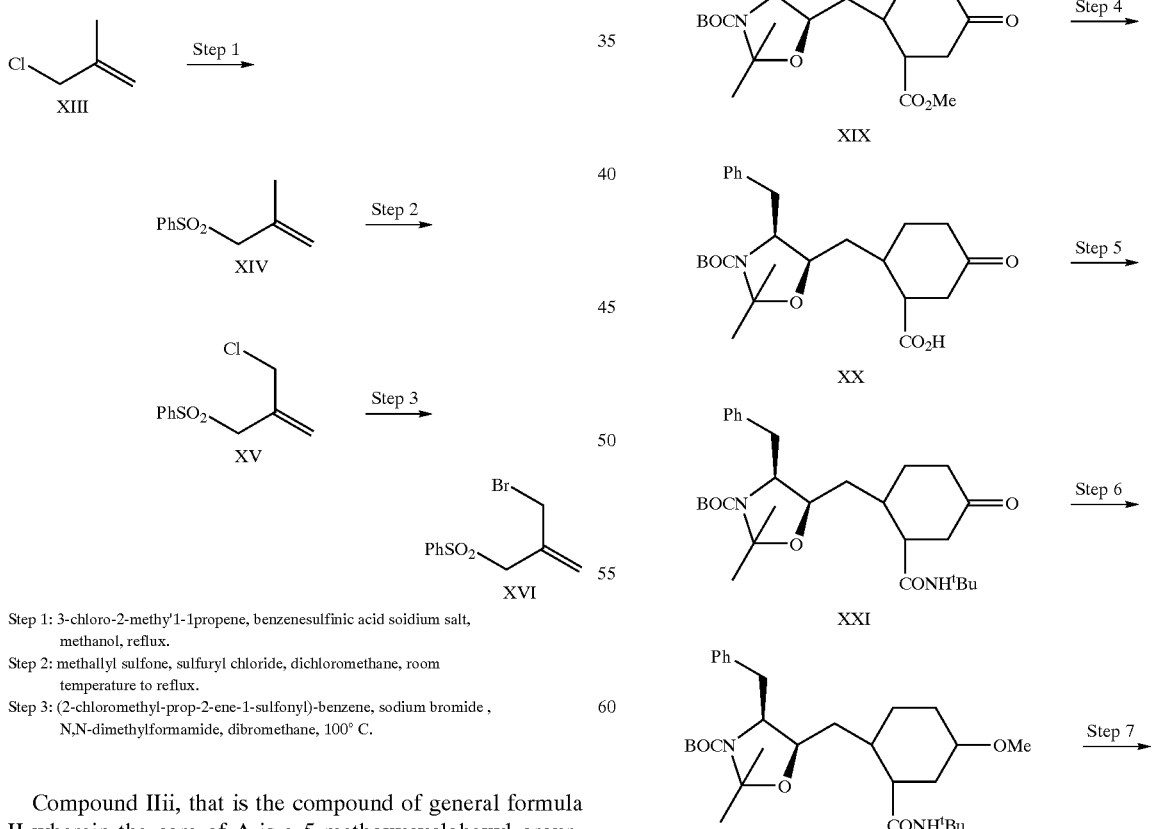

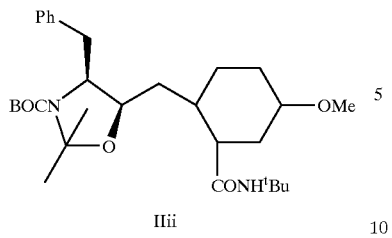

IIii

Step 1: ozone, dichloromethane, methanol, -78° C; triphenylphosphine, -78° C. to room temperature.
Step 2: paratoluene sulfonic acid monohydrate, toluene, Dean-Stark, reflux.
Step 3: hydrogen, palladium or charcoal, ethyl acetate, room temperature.
Step 4: lithium hydroxide, tetrahydrofuran, water, room temperature.
Step 5: tert-butyl amine, 1-(3-dimethylaminopropyl)-3-ethylcarbodiimide hydrochloride, 1-hydroxybenzotriazole, dichloromethane, 0° C. to room temperature.
Step 6: sodium borohydride, cerium (III) chloride hexahydrate, methanol, -78° C. to room temperature.
Step 7: sodium hydride, methyl iodide, N,N-dimethyl formamide, 0° C. to room temperature.

Compound IIiii, that is the compound of general formula II wherein the core of A is a 4-methoxycyclohexyl group, can be obtained from intermediate XXIII according to the route depicted in scheme E.

Scheme E

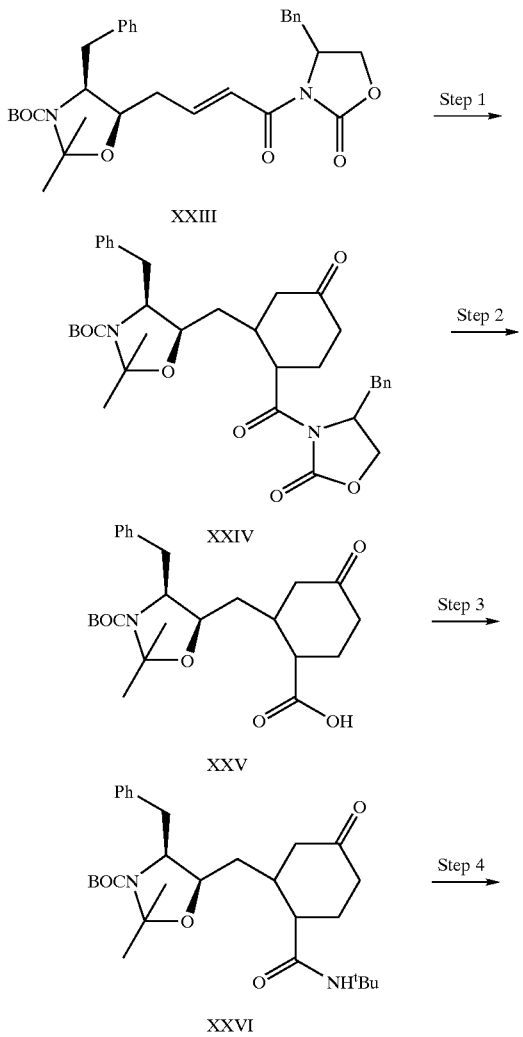

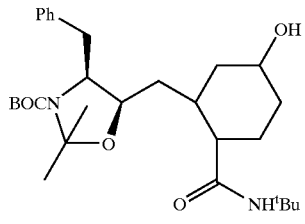

XXVII

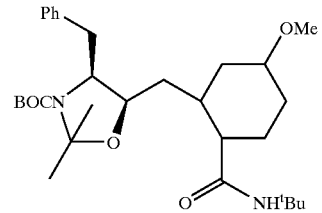

IIiii

Step 1: trimethyl-(1-methylene-allyloxy)-silane, diethylaauminium chloride, dichloromethane, -78° C.
Step 2: lithium hydroxide, 30% aqueous hydrogen peroxide, tetrahydrofuran, water, 0° C. to room temperature.
Step 3: tert-butyl amine, 1-(3-dimethylaminopropyl)-3-ethylcarbodiimide hydrochloride, 1-hydroxybenzotriazole, dichloromethane, 0° C. to room temperature.
Step 4: L-selectride, tetrahydrofuran, -78° C.
Step 5: sodium hydride, methyl iodide, N-N-dimethyl formamide, 0° C. to room temperature.

Compounds of general formula I in which A is A1 and R2 is lower alkoxy can be prepared by analogous methods to those described in schemes D and E, by alkylation of compounds XXII or XXVII with C2–C7 alkyl halides or related reagents described in the art for the formation of alkyl ethers. For example see J. March (1992) "Advanced Organic Chemistry: Reactions, Mechanisms and Structure", 4th ed. John Wiley & Sons.

Compound IIiv, that is the compound of general formula II wherein the core of A is a cyclohexyl group, can be obtained according to the route depicted in scheme F:

Scheme F

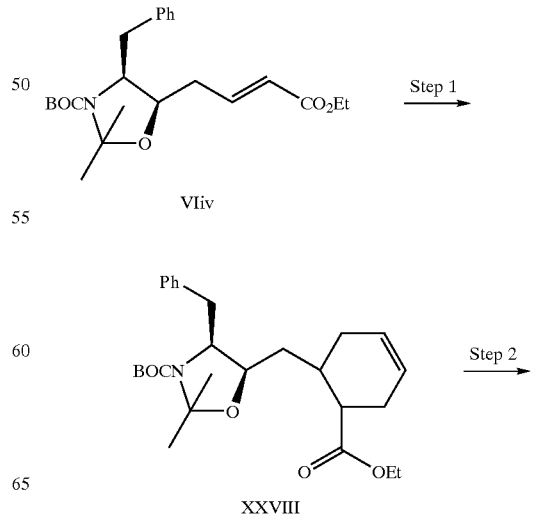

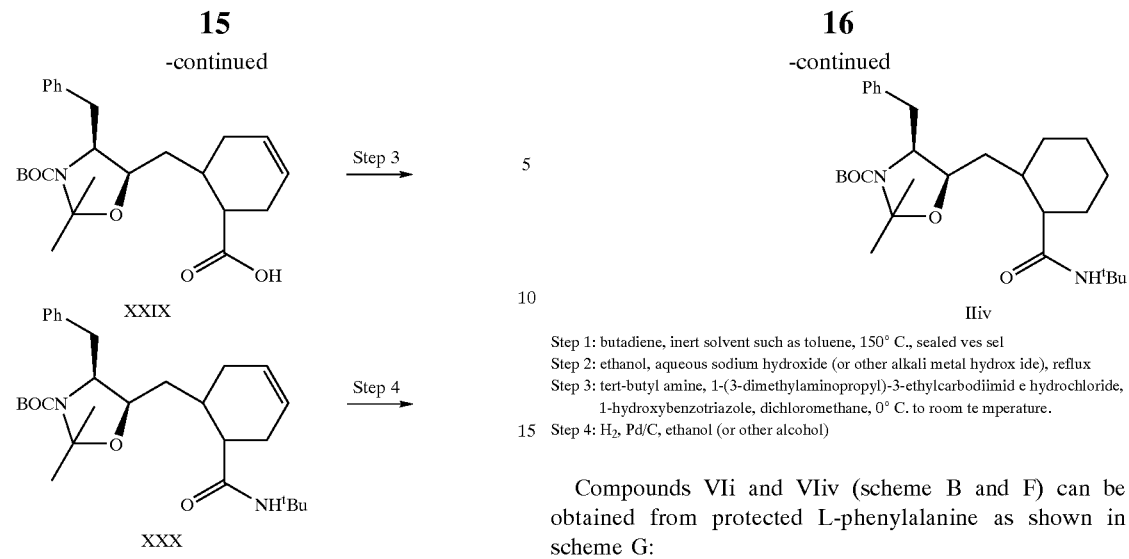

Step 1: butadiene, inert solvent such as toluene, 150° C., sealed vessel
Step 2: ethanol, aqueous sodium hydroxide (or other alkali metal hydroxide), reflux
Step 3: tert-butyl amine, 1-(3-dimethylaminopropyl)-3-ethylcarbodiimide hydrochloride, 1-hydroxybenzotriazole, dichloromethane, 0° C. to room temperature.
Step 4: H₂, Pd/C, ethanol (or other alcohol)

Compounds VIi and VIiv (scheme B and F) can be obtained from protected L-phenylalanine as shown in scheme G:

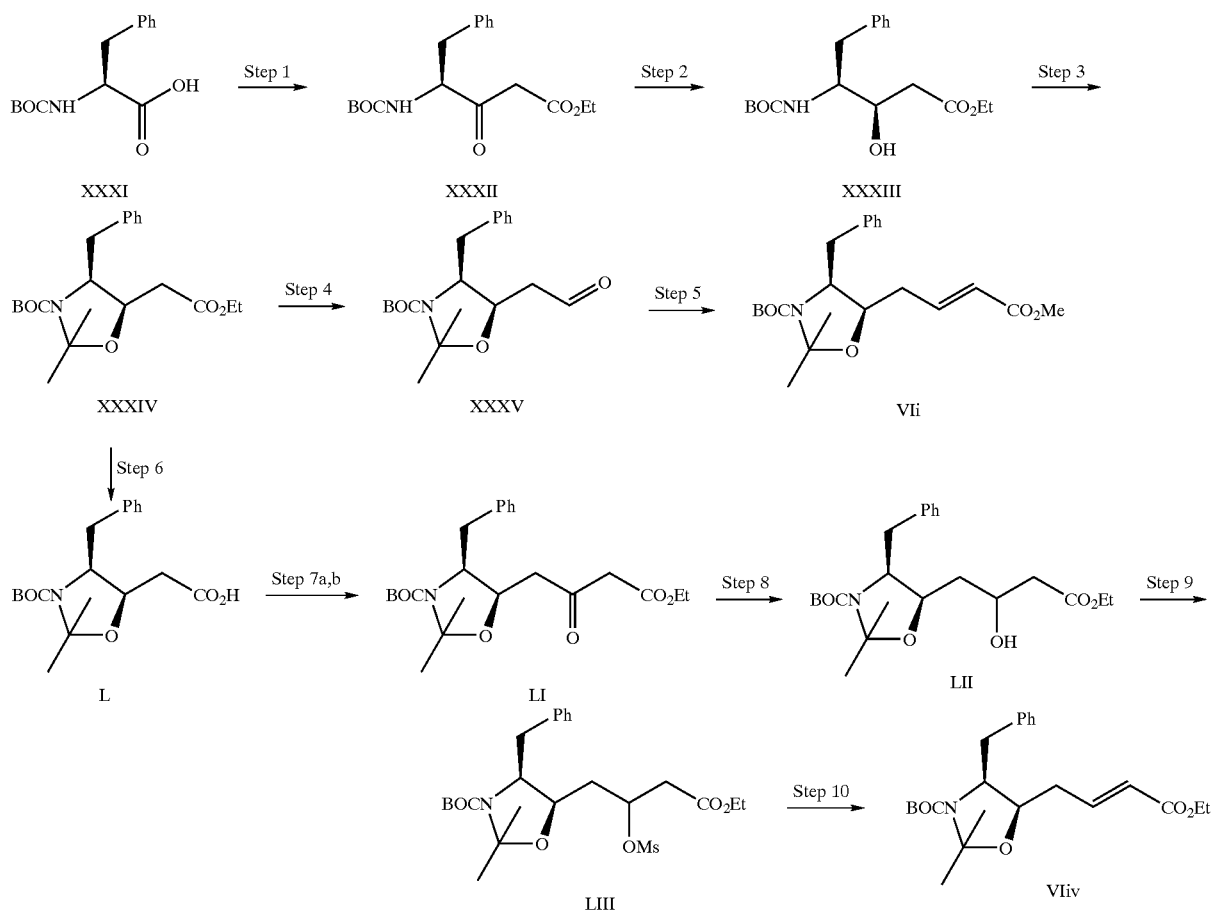

Step 1: 1,1'-carbonyldiimidazole, tetrahydrofuran, 0° C.; mono-ehtyl malonate, isopropyl magnesiumchloride, tetrahydrofuran, 0° C.
Step 2: sodium borohydride, ethanol, 0° C.
Step 3: 2.2-dimethoxy-propane, tetrahydrofuran, paratoluene sulfonic acid monohydrate, 55° C.
Step 4: diisobutyl aluminium hydride, toluene, -78° C.
Step 5: carboxymethylene triphenylphosphorane, tetrahydrofuran, room temperature.
Step 6: ethanol (or other alcohol or water miscible ehter such as tetrahydrofuran), water, sodium hydroxide (or other alkali metal hydroxide), ambient temperature.
Step 7a: carbonyl diimidazole, tetrahydrofuran, 0° C.
Step 7b: mono-ethyl malonate, iso-propyl magnesium chloride, tetrahydrofuran, 0° C.
Step 8: sodium borohydride, ethanol, acetic acid, 15° C.
Step 9: methanesulphonyl chloride, pyridine, 15° C.
Step 10: 1,8-diazobicyclo[5,4,0]undec-7-ene, dichloromethane, 15° C.

Compound XXIII (scheme E) can be obtained from intermediate XXXV and commercially available oxazolidinone XXXVI according to the route depicted in scheme H):

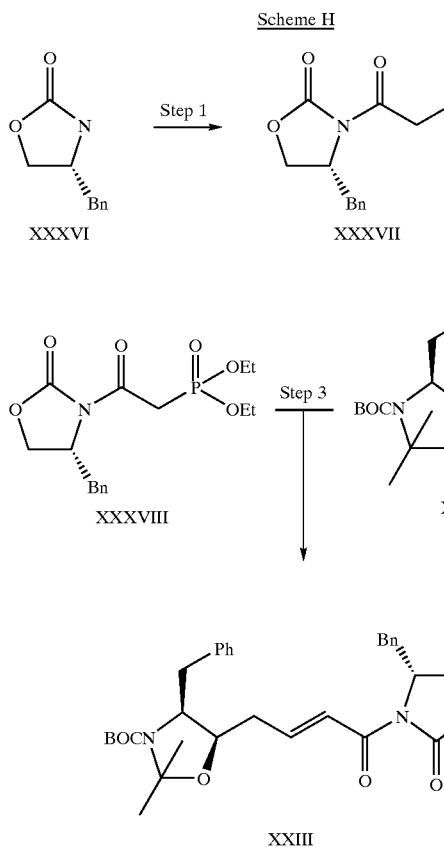

Step 1: n-butyl lithium, bromo-acetyl bromide, tetrahydrofuran, -78° C. to room temperature.
Step 2: triethylphosphite, toluene, reflux.
Step 3: 1,8-diazabicyclo[5.4.0]undec-7-ene, lithium chloride, acetonitrile, room temperature.

The BOC-protected amino acids required in Scheme A, step 2, can be obtained according to the following procedure (Scheme I):

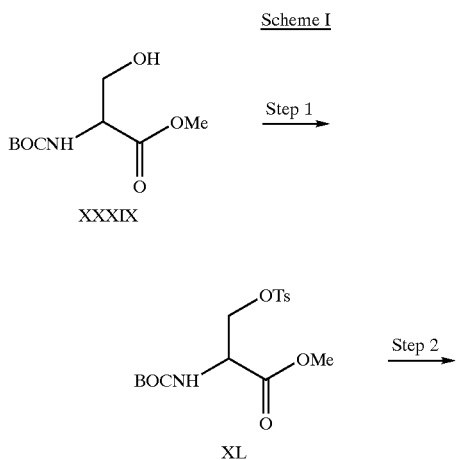

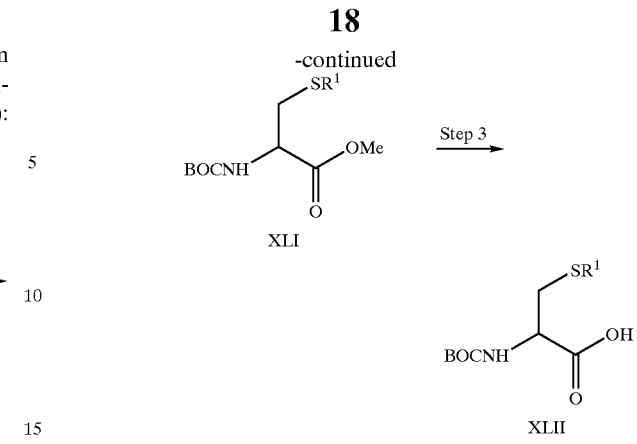

Step 1: Tosyl chloride, triethylamine, 4-(dimethylamino)pyridine, dichloromethane, -10° C.
Step 2: Aryl thiol, sodium hydride, N,N-dimethyl formamide, room temperature.
Step 3: sodium hydroxide, methanol/water, room temperature.

ASSAY METHODS

HIV Protease Inhibition Assay

HIV protease inhibitory activity was assessed using an adaptation of the method of Matayoshi. et al. [Matayoshi E. D. et al (1990). Science. 247. 954–958]

Crude HIV-1 protease was prepared from *E. coli* pPTΔN. Cultures were grown at 30° C. in M9 medium supplemented with 0.2% casamino acids, 100 µg/ml ampicillin and 25 µg/ml thiamine until $OD_{600}$=0.5–0.6, and the temperature was raised to 42° C. to induce expression of the protease. After 1.5 hours, the cells were harvested and the pellets stored at −70° C. until required.

The protease was prepared by lysis of the cells in a French pressure cell followed by precipitation of the enzyme with ammonium sulfate at 30% saturation.

The assay was based on intramolecular fluorescence energy transfer using a quenched fluorogenic substrate DABCYL-Ser.Gln.Asn.Tyr.Pro.Ile.Val.Gln.-EDANS, the peptide sequence of which was derived from one of the natural polypeptide processing sites of HIV-1 protease.

The peptide substrate was dissolved in spectroscopic grade dimethyl sulphoxide (DMSO) to give a stock solution of 500 µM. Inhibitors were dissolved in a 1:9 mixture of DMSO:0.1% aqueous Tween 20 to give inhibitor concentrations 20× more concentrated than the desired final concentration. The assay buffer comprised 0.1M sodium acetate pH 4.7, 8 mM EDTA, 0.2 M NaCl.

10 µl HIV-1 protease diluted in a 1:1 mixture of 0.1% Tween: assay buffer (concentration adjusted to give approximately 20% substrate turnover) was added to a mixture comprising 455 µl assay buffer, 25 µl inhibitor solution, 10 µl substrate solution. Tubes were incubated for 2 hours at 37° C. and the reaction was terminated by the addition of 500 µl of a 2:1 mixture of DMSO: 50 mM Tricine pH 8.5. Fluorescence was measured in a fluorescence spectrophotometer, excitation λ=340 nm, emission λ=492 nm.

Antiviral Assay Method

Anti-HIV antiviral activity was assessed using an adaptation of the method of Pauwels et al. [Pauwels et al., 1988, J. Virol. Methods 20: 309–321]. The method is based on the ability of compounds to protect HIV-infected T lymphoblastoid cells (MT4 cells) from cell-death mediated by the infection. The endpoint of the assay was calculated as the concentration of compound at which the cell viability of the culture was preserved by 50% ('50% inhibitory concentration', $IC_{50}$). The cell viability of a culture was determined by the uptake of soluble, yellow 3-[4,5-dimethylthiazol-2-yl]-2,5-diphenyltetrazolium bromide (MTT) and its reduction to a purple insoluble formazan salt. After solubilization, spectrophotometric methods were employed to measure the amount of formazan product. MT4 cells were prepared to be in logarithmic-phase growth and a total of $2 \times 10^6$ cells infected with either the wild type or site directed mutant clones of HIV-HXB2 at a multiplicity of approximately 0.0001 infectious units of virus per cell in a total volume of between 200–500 µl. The cells were incubated with virus for one hour at 37° C. then washed in 0.01 M phosphate buffered saline, pH 7.2, and resuspensed in culture medium for incubation in culture with serial dilutions of test compound. The culture medium used was RPMI 1640 without phenol red, supplemented with penicillin, streptomycin, L-glutamine and 10% fetal calf serum (GM 10).

Test compounds were prepared as 2 mM solutions in dimethyl sulphoxide (DMSO). Four replicate, serial 2-fold dilutions in GM10 were then prepared and 50 microlitre amounts placed in 96-well plates over a final concentration range of 625–1.22 nm. Fifty microlitres GM10 and $3.75 \times 10^4$ infected cells were then added to each well. Control cultures containing no cells (blank), uninfected cells (100% viability; 4 replicates) and infected cells without compound (total virus-mediated cell death; 4 replicates) were also prepared. The cultures were then incubated at 37° C. in a humidified atmosphere of 5% $CO_2$ in air for 5 days.

A fresh solution of 5 mg/mL MTT was prepared in 0.01 M phosphate buffered saline, pH 7.2 and 20 µL added to each culture. The cultures were further incubated as before for 2 hours. They were then mixed by pipetting up and down, and 170 microlitres of Triton X-100 in acidified isopropanol (10% v/v Triton X-100 in 1:250 mixture of concentrated HCl in isopropanol) were added and the cultures were mixed again by pipetting up and down. When the formazan deposit was fully solubilised by further mixing, the absorbance (OD) of the cultures was measured at 540 nm and 690 nm wavelength (690 nm readings were used as blanks for artefacts between wells). The percent protection for each treated culture was then calculated from the equation:

$$\% \text{ Protection} = \frac{(OD \text{ drug-treated cultures}) - (OD \text{ untreated virus control cultures})}{(OD \text{ uninfected cultures}) - (OD \text{ untreated virus control cultures})} \times 100\%$$

The $IC_{50}$ was then obtained from graph plots of percentage protection versus $\log_{10}$ drug concentration.

The $IC_{50}$ of the compounds of the present invention is as a rule up to 10,000 nM, preferably up to 60 nM, and most preferably up to 10 nM.

$IC_{50}$ values for selected compounds are shown in the following table:

The compounds of the present invention, as well as their pharmaceutically usable acid addition salts, can be used as medicaments, e.g. in the form of pharmaceutical preparations. The pharmaceutical preparations can be administered orally, e.g. in the form of tablets, coated tablets, dragées, hard and soft gelatin capsules, solutions, emulsions or suspensions. The administration can, however, also be effected rectally, e.g. in the form of suppositories, or parenterally, e.g. in the form of injection solutions.

The compounds of the present invention and their pharmaceutically usable acid addition salts can be processed with pharmaceutically inert, inorganic or organic excipients for the production of tablets, coated tablets, dragees and hard gelatin capsules. Lactose, corn starch or derivatives thereof, talc, stearic acid or its salts etc. can be used as such excipients e.g. for tablets, dragees and hard gelatine capsules.

Suitable excipients for soft gelatine capsules are e.g. vegetable oils, waxes, fats, semi-solid and liquid polyols etc.

Suitable excipients for the manufacture of solutions and syrups are e.g. water, polyols, saccharose, invert sugar, glucose etc.

Suitable excipients for injection solutions are e.g. water, alcohols, polyols, glycerol, vegetable oils etc.

Suitable excipients for suppositories are e.g. natural or hardened oils, waxes, fats, semi-liquid or liquid polyols etc.

Moreover, the pharmaceutical preparations can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The dosage can vary within wide limits and will, of course, be fitted to the individual requirements in each particular case. In general, in the case of oral administration a daily dosage of about 10 to 2500 mg per person of a compound of formula I should be appropriate, although the above upper limit can also be exceeded when necessary.

The daily dosage can be administered as a single dosage or in divided dosages. The treatment may be in conjunction with the administration of one or more additional therapeutically active substance(s), and such administration may be concurrent or sequential with respect to that of the compounds of formula I. Thus, concurrent administration, as used herein, includes administration of the agents in conjunction or combination, together, or before or after each other.

|  | Example | | | | | | | | | | | | |
|---|---|---|---|---|---|---|---|---|---|---|---|---|---|
|  | 1 | 2 | 7 | 10 | 13 | 14 | 15 | 20 | 21 | 23 | 27 | 29 | 30 |
| Enzyme $IC_{50}$ (nM) | 0.31 | 1.5 | 0.42 | 0.3 | 0.44 | 0.2 | 1.5 | 0.2 | 0.31 | 0.55 | 0.2 | 0.41 | 0.6 |
| Antiviral $IC_{50}$ (nM) | 29 | 230 | 35.8 | 28 |  | 20.9 | 27.0 | 21 |  | 13 | 8.3 | 73 | 173 |

EXPERIMENTAL PART

Scheme A 2-(3-Amino-2-hydroxy-4-phenyl-butyl)-5-methoxy-cyclohexanecarboxylic Acid tert-Butylamide

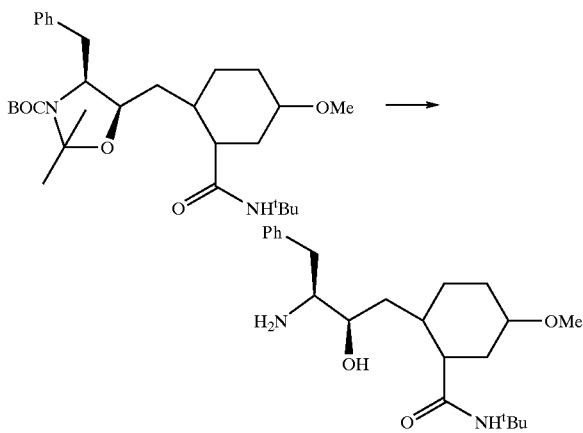

To an ice-cooled solution of 4-benzyl-5-(2-tert-butylcarbamoyl-4-methoxy-cyclohexylmethyl)-2,2-dimethyl-oxazolidine-3-carbocylic acid tert-butyl ester (358 mg, 0.69 mmol) in dichloromethane (3 ml) and trifluoroacetic acid (3 ml), three drops of water were added. The resulting mixture was stirred at 0° C. for 1 hour and then concentrated in vacuo. The residue was co-evaporated twice with toluene, re-dissolved in dichloromethane, washed with a 5% aqueous sodium hydrogen carbonate solution and brine, dried (anhydrous magnesium sulfate) and concentrated in vacuo to give 2-(3-amino-2-hydroxy-4-phenyl-butyl)-5-methoxy-cyclohexanecarboxylic acid tert-butylamine as a white foam (200 mg) which was used in the next step without further purification.

In an analogous manner, the following compounds have been made:

[1-[1-Benzyl-3-(2-tert-butylcarbamoyl-4-methoxy-cyclohexyl)-2-hydroxy-propylcarbamoyl]-2-(naphthalen-2-ylsulfanyl)-ethyl]-carbamic Acid tert-Butyl Ester

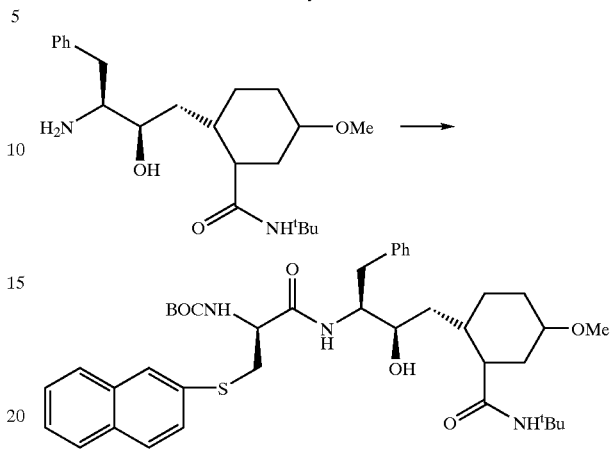

An ice-cooled mixture of 2-(3-amino-2-hydroxy-4-phenyl-butyl)-5-methoxy-cyclohexanecarboxylic acid tert-butylamine (93 mg, 0.247 mmol) and 2-tert-butoxycarbonylamino-3-(naphthalen-2-ylsulfanyl)-propionic acid (95 mg, 0.27 mmol) in dichloromethane (2 ml) and N,N'-dimethylformamide (1 ml) was treated sequentially with N-ethyl morpholine (144 μl, 1 mmol),1-hydroxybenzotriazole hydrate (57 mg, 0.31 mmol) and N-ethyl-N'-(3-dimethylaminopropyl)carbodiimide hydrochloride (63 mg, 0.30 mmol). The resulting mixture was allowed to warm to room temperature, stirred overnight and finally concentrated in vacuo. The residue was dissolved in ethyl acetate, washed sequentially with 5% aqueous sodium hydrogen carbonate solution, water, 2N hydrochloric acid-

| Name | Structure | [M + H]⁺ |
|---|---|---|
| 2-(3-Amino-2-hydroxy-4-phenyl-butyl)-4-methyl-cyclopentanecarboxylic acid tert-butylamide | 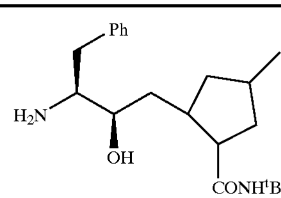 | 347 |
| 2-(3-Amino-2-hydroxy-4-phenyl-butyl)-4-methoxy-cyclohexanecarboxylic acid tert-butylamide | 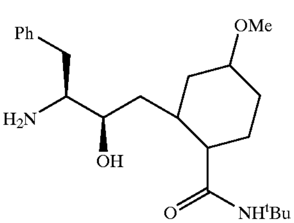 | 377 |
| 2-(3-Amino-2-hydroxy-4-phenyl-butyl)-cyclohexanecarboxylic acid tert-butylamide | | 347 | and water. The organic phase was dried (anhydrous magnesium sulfate) and concentrated in vacuo to give, after purification by flash chromatography on silica gel (dichloromethane/methanol: 98/2), [1-[1-benzyl-3-(2-tert-butylcarbamoyl-4-methoxy-cyclohexyl)-2-hydroxy-propylcarbamoyl]-2-(naphthalen-2-ylsulfanyl)-ethyl]-carbamic acid tert-butyl ester (136 mg, 78%) as a white foam.

The following compounds were prepared in a similar manner by coupling the appropriate acids and amines:

| Structure | Name | [M + H]+ |
|---|---|---|
| 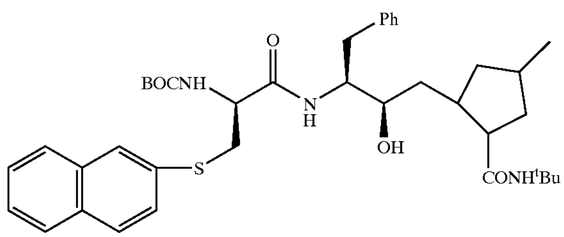 | [1-[1-Benzyl-3-(2-tert-butylcarbamoyl-4-methyl-cyclopentyl)-2-hydroxy-propylcarbamoyl]-2-(naphthalen-2-ylsulfanyl)-ethyl]-carbamic acid tert-butyl ester | 676 |
| 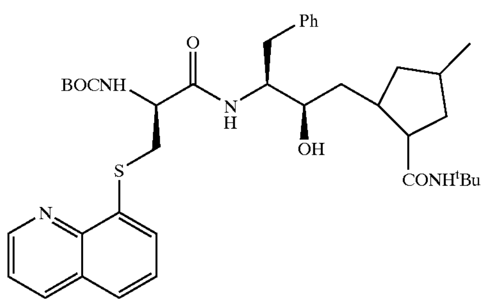 | [1-[1-Benzyl-3-(2-tert-butylcarbamoyl-4-methyl-cyclopentyl)-2-hydroxy-propylcarbamoyl]-2-(quinolin-8-ylsulfanyl)-ethyl]-carbamic acid tert-butyl ester | 677 |
| 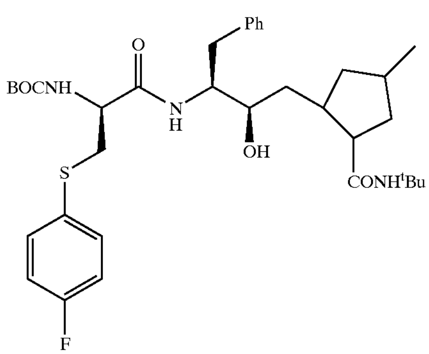 | [1-[1-Benzyl-3-(2-tert-butylcarbamoyl-4-methyl-cyclopentyl)-2-hydroxy-propylcarbamoyl]-2-(4-fluoro-phenylsulfanyl)-ethyl]-carbamic acid tert-butyl ester | 644 |
| 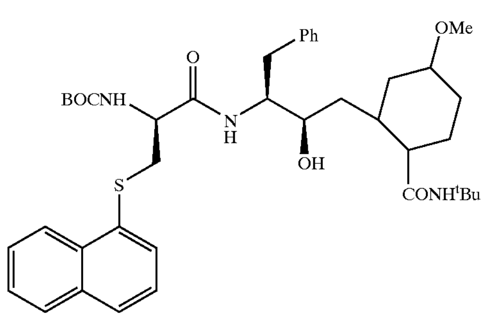 | [1-[1-Benzyl-3-(2-tert-butylcarbamoyl-5-methoxy-cyclohexyl)-2-hydroxy-propylcarbamoyl]-2-(naphthalen-1-ylsulfanyl)-ethyl]-carbamic acid tert-butyl ester | 706 |

-continued

| Structure | Name | [M + H]+ |
|---|---|---|
| 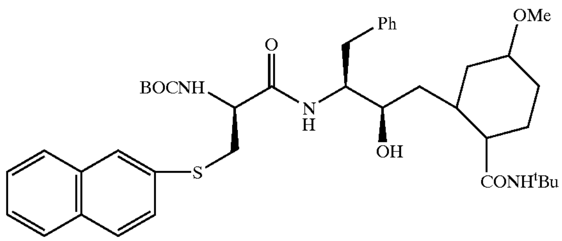 | [1-[1-Benzyl-3-(2-tert-butylcarbamoyl-5-methoxy-cyclohexyl)-2-hydroxy-propylcarbamoyl]-2-(naphthalen-2-ylsulfanyl)-ethyl]-carbamic acid tert-butyl ester | 706 |
| 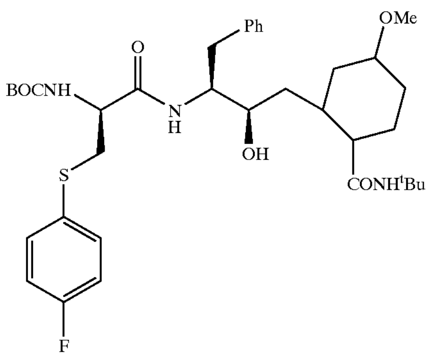 | [1-[1-Benzyl-3-(2-tert-butylcarbamoyl-5-methoxy-cyclohexyl)-2-hydroxy-propylcarbamoyl]-2-(4-fluoro-phenylsulfanyl)-ethyl]-carbamic acid tert-butyl ester | 674 |
| 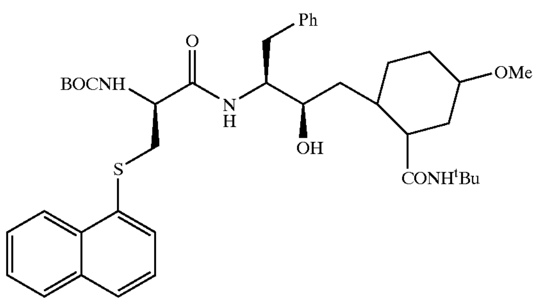 | [1-[1-Benzyl-3-(2-tert-butylcarbamoyl-4-methoxy-cyclohexyl)-2-hydroxy-propylcarbamoyl]-2-(naphthalen-1-ylsulfanyl)-ethyl]-carbamic acid tert-butyl ester | 706 |
| 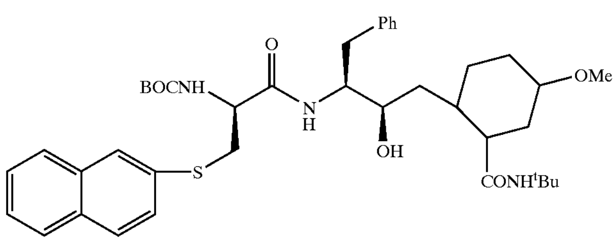 | [1-[1-Benzyl-3-(2-tert-butylcarbamoyl-4-methoxy-cyclohexyl)-2-hydroxy-propylcarbamoyl]-2-(naphthalen-2-ylsulfanyl)-ethyl]-carbamic acid tert-butyl ester | 706 |
| 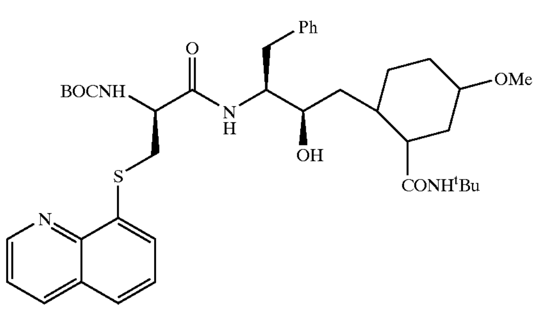 | [1-[1-Benzyl-3-(2-tert-butylcarbamoyl-4-methoxy-cyclohexyl)-2-hydroxy-propylcarbamoyl]-2-(quinolin-8-ylsulfanyl)-ethyl]-carbamic acid tert-butyl ester | 707 |

| Structure | Name | [M + H]+ |
|---|---|---|
| 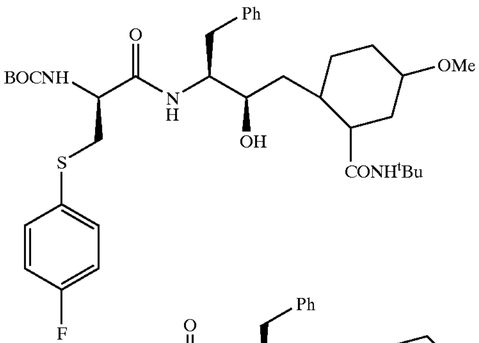 | [1-[1-Benzyl-3-(2-tert-butylcarbamoyl-4-methoxy-cyclohexyl)-2-hydroxy-propylcarbamoyl]-2-(4-fluoro-phenylsulfanyl)-ethyl]-carbamic acid tert-butyl ester | 674 |
| 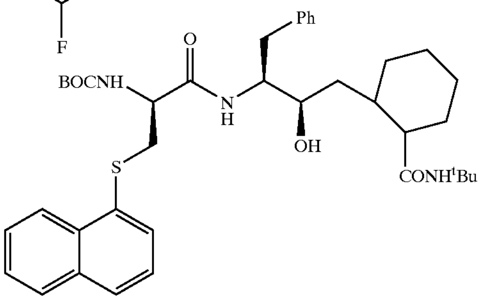 | [1-[1-Benzyl-3-(2-tert-butylcarbamoyl-cyclohexyl)-2-hydroxy-propylcarbamoyl]-2-(naphthalen-1-ylsulfanyl)-ethyl]-carbamic acid tert-butyl ester | 676 |

EXAMPLE 1

[1-[1-Benzyl-3-(2-tert-butylcarbamoyl-4-methoxy-cyclohexyl)-2-hydroxy-propylcarbamoyl]-2-(naphthalen-2-ylsulfanyl)-ethyl]-carbamic Acid tert-Butyl Ester

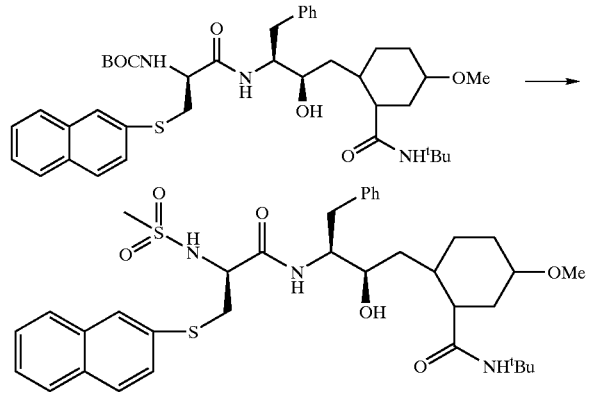

To a solution of [1-[1-benzyl-3-(2-tert-butylcarbamoyl-4-methoxy-cyclohexyl)-2-hydroxy-propylcarbamoyl]-2-(naphthalen-2-ylsulfanyl)-ethyl]-carbamic acid tert-butyl ester (135 mg, 0.19 mmol) in dichloromethane (3 ml) at 0° C. was added trifluoroacetic acid (2 ml) and the resulting mixture was allowed to warm to room temperature over 2 hours, concentrated in vacuo and then co-evaporated twice with toluene. The residue was dissolved in ethyl acetate, washed with aqueous 5% sodium hydrogen carbonate solution and water, dried (anhydrous magnesium sulfate) and concentrated in vacuo to a white foam. The foam was dissolved in dichloromethane (2 ml) at 0° C. and treated with N-ethyl morpholine (48 μl, 0.38 mmol) and methanesulfonic anhydride (66 mg, 0.38 mmol). The resulting mixture was stirred at 0° C. for 1 hour and then concentrated in vacuo. The residue was dissolved in ethyl acetate and the resulting solution washed with 2N hydrochloric acid and water, dried (anhydrous magnesium sulfate) and concentrated in vacuo to give, after purification by flash chromatography on silica gel (dichloromethane/methanol: 98/2 to 96/4) of 2-{2-hydroxy-3-[2-methanesulfonylamino-3-(naphthalen-2-ylsulfanyl)-propionylamino]-4-phenyl-butyl}-5-methoxy-cyclohexanecarboxylic acid tert-butylamide (88 mg, 68%) as a white foam. Mass spectrum, 685 [M+H]+.

| Ex. | Structure | Name | [M + H]+ |
|---|---|---|---|
| 2 | 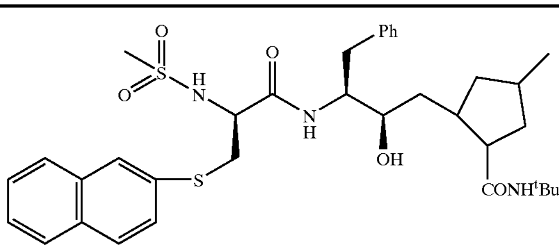 | 2-{2-Hydroxy-3-[2-methanesulfonylamino-3-(naphthalen-2-ylsulfanyl)-propionylamino]-4-phenyl-butyl}-4-methyl-cyclopentanecarboxylic acid tert-butylamide | 654 |

-continued

| Ex. | Structure | Name | [M + H]+ |
|---|---|---|---|
| 3 | 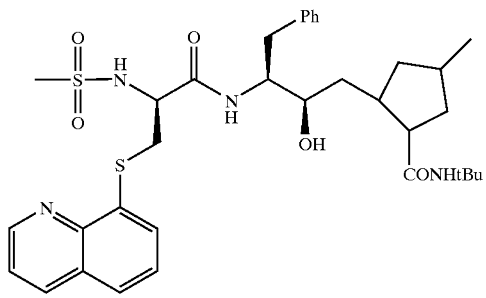 | 2-{2-Hydroxy-3-[2-methanesulfonylamino-3-(quinolin-8-ylsulfanyl)-propionylamino]-4-phenyl-butyl}-4-methyl-cyclopentanecarboxylic acid tert-butylamide | 655 |
| 4 | 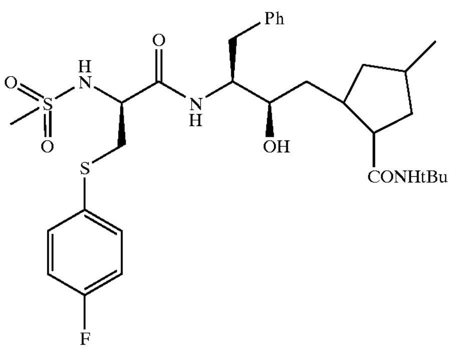 | 2-{3-[3-(4-Fluoro-phenylsulfanyl)-2-methanesulfonyl-amino-propionylamino]-2-hydroxy-4-phenyl-butyl}-4-methyl-cyclopentanecarboxylic acid tert-butylamide | 622 |
| 5 | 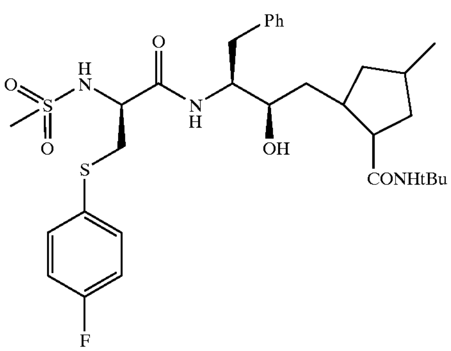 | 2-{3-[3-(4-Fluoro-phenylsulfanyl)-2-methanesulfonyl-amino-propionylamino]-2-hydroxy-4-phenyl-butyl}-4-methyl-cyclopentanecarboxylic acid tert-butylamide | 622 |
| 6 | 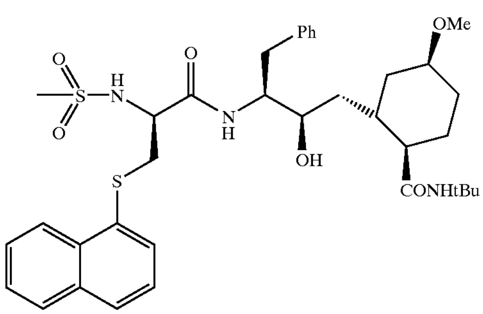 | 2-{2-Hydroxy-3-[2-methanesulfonylamino-3-(naphthalen-1-ylsulfanyl)-propionylamino]-4-phenyl-butyl}-4-methoxy-cyclohexanecarboxylic acid tert-butylamide | 684 |
| 7 | 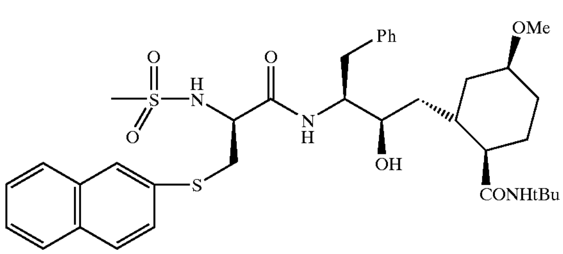 | N-tert-Butyl-[2-hydroxy-3-[[N2-(methanesulfonyl)-S-(2-naphthyl)-D-cysteinyl]amino]-4-phenylbutyl]-4-methoxy-1-cyclohexanecarboxamide | 684 |

-continued

| Ex. | Structure | Name | [M + H]+ |
|---|---|---|---|
| 8 | 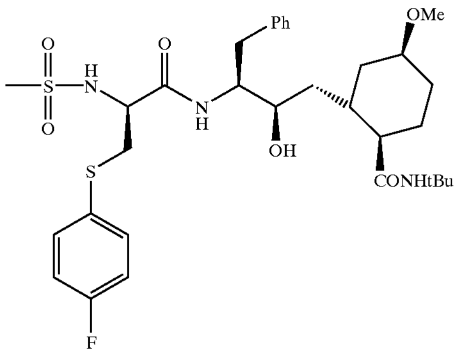 | 2-{3-[3-(4-Fluoro-phenylsulfanyl)-2-methanesulfonyl-amino-propionylamino]-2-hydroxy-4-phenyl-butyl}-4-methoxy-cyclohexanecarboxylic acid tert-butylamide | 652 |
| 9 | 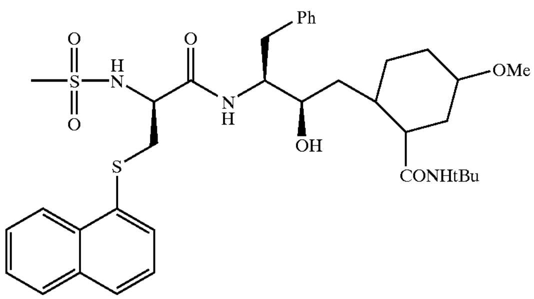 | 2-{2-Hydroxy-3-[2-methanesulfonylamino-3-(naphthalen-1-ylsulfanyl)-propionylamino]-4-phenyl-butyl}-5-methoxy-cyclohexanecarboxylic acid tert-butylamide | 684 |
| 10 | 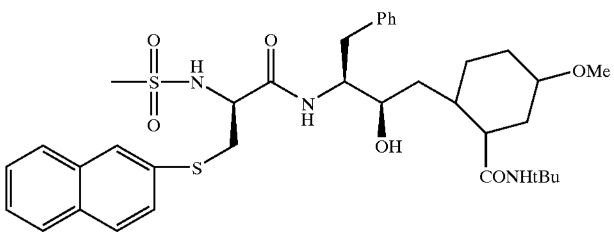 | 2-{2-Hydroxy-3-[2-methanesulfonylamino-3-(naphthalen-2-ylsulfanyl)-propionylamino]-4-phenyl-butyl}-5-methoxy-cyclohexanecarboxylic acid tert-butylamide | 684 |
| 11 | 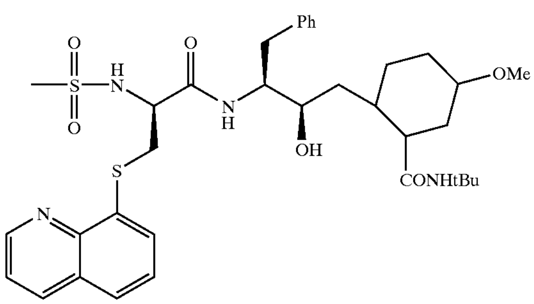 | 2-{2-Hydroxy-3-[2-methanesulfonylamino-3-(quinolin-8-ylsulfanyl)-propionylamino]-4-phenyl-butyl}-5-methoxy-cyclohexanecarboxylic acid tert-butylamide | 685 |
| 12 | 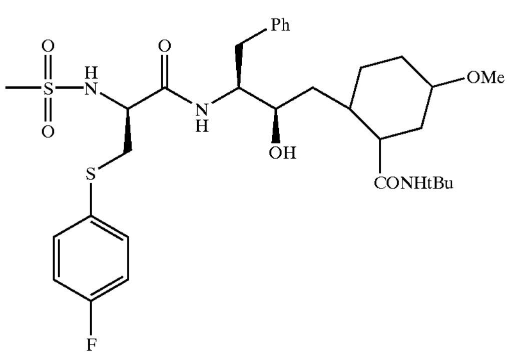 | 2-{3-[3-(4-Fluoro-phenylsulfanyl)-2-methanesulfonyl-amino-propionylamino]-2-hydroxy-4-phenyl-butyl}-5-methoxy-cyclohexanecarboxylic acid tert-butylamide | 652 |

| Ex. | Structure | Name | [M + H]+ |
|---|---|---|---|
| 13 | 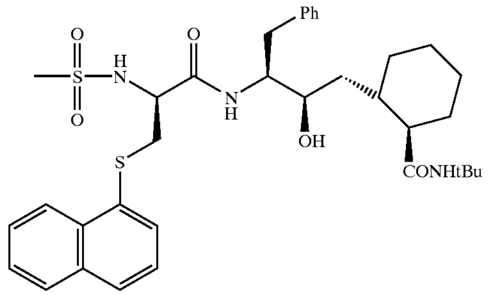 | 2-{2-Hydroxy-3-[2-methanesulfonylamino-3-(naphthalen-1-ylsulfanyl)-propionylamino]-4-phenyl-butyl}-cyclohexanecarboxylic acid tert-butylamide | 654 |

EXAMPLE 14
2-{2-Hydroxy-3-[2-methanesulfonylamino-3-(naphthalene-2-sulfinyl)-propionylamino]-4-phenyl-butyl}-5-methoxy-cyclohexanecarboxylic Acid tert-Butylamide

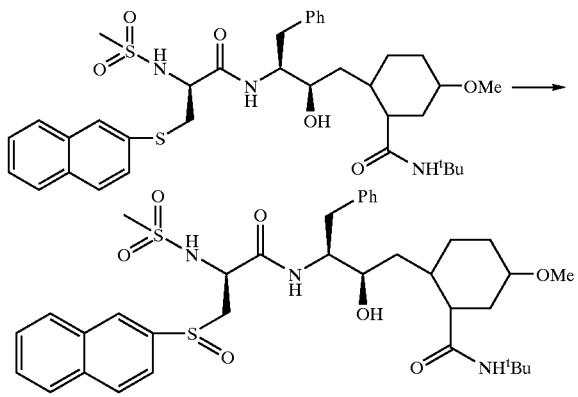

A solution of 2-{2-Hydroxy-3-[2-methanesulfonylamino-3-(naphthalen-2-ylsulfanyl)-propionylamino]-4-phenyl-butyl}-5-methoxy-cyclohexanecarboxylic acid tert-butylamide (80 mg, 0.117 mmol) in dichloromethane (3 ml) was cooled to −10° C. A solution of meta-chloroperbenzoic acid in dichloromethane (2 ml) was added and the mixture stirred at −10° C. for 30 minutes. The solution was then washed with 5% aqueous sodium hydrogen carbonate solution, dried (anhydrous magnesium sulfate) and concentrated in vacuo to give, after purification by flash chromatography on silica gel (dichloromethane/methanol: 97/3 2-{2-Hydroxy-3-[2-methanesulfonylamino-3-(naphthalen-2-sulfinyl)-propionylamino]-4-phenyl-butyl}-5-methoxy-cyclohexanecarboxylic acid tert-butylamide (65 mg, 70%) as a white solid. Mass spectrum, 701 [M+H]+. The following compounds were prepared in a similar manner, by oxidation of the appropriate sulphide:

| Ex. | Structure | Name | [M + H]+ |
|---|---|---|---|
| 15 | 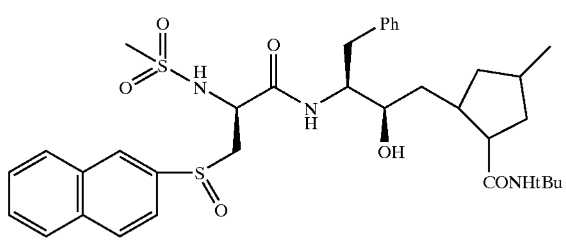 | 2-{2-Hydroxy-3-[2-methanesulfonylamino-3-(naphthalene-2-sulfinyl)-propionylamino]-4-phenyl-butyl}-4-methyl-cyclopentanecarboxylic acid tert-butylamide | 670 |
| 16 | 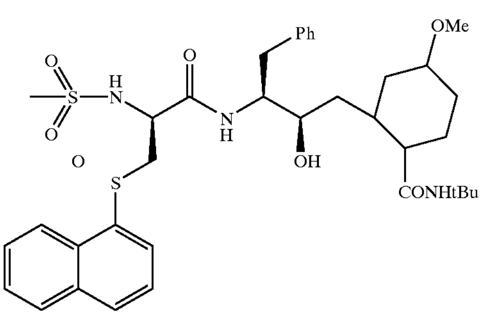 | 2-{2-Hydroxy-3-[2-methanesulfonylamino-3-(naphthalene-1-ylsulfinyl)-propionylamino]-4-phenyl-butyl}-4-methoxy-cyclohexanecarboxylic acid tert-butylamide | 700 |

| Ex. | Structure | Name | [M + H]⁺ |
|---|---|---|---|
| 17 | 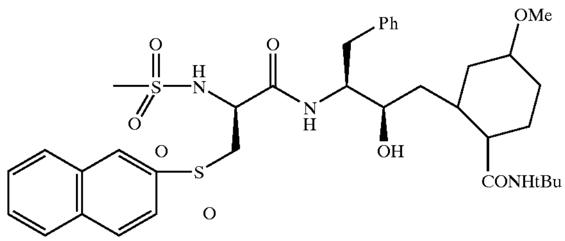 | 2-{2-Hydroxy-3-[2-methanesulfonylamino-3-(naphthalene-2-sulfinyl)-propionylamino]-4-phenyl-butyl}-4-methoxy-cyclohexanecarboxylic acid tert-butylamide | 700 |
| 18 | 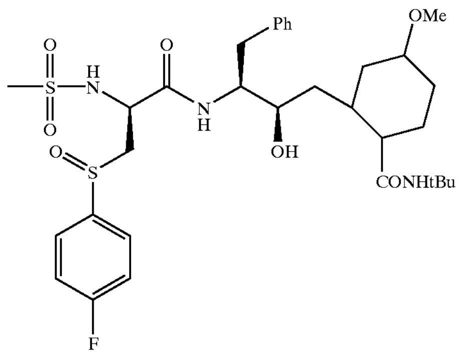 | 2-{3-[3-(4-Fluoro-benzenesulfinyl)-2-methanesulfonyl-amino-propionylamino]-2-hydroxy-4-phenyl-butyl}-4-methoxy-cyclohexanecarboxylic acid tert-butylamide | 668 |
| 19 | 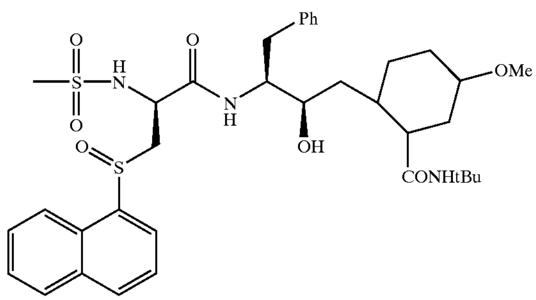 | 2-{2-Hydroxy-3-[2-methanesulfonylamino-3-(naphthalene-1-sulfinyl)-propionylamino]-4-phenyl-butyl}-5-methoxy-cyclohexanecarboxylic acid tert-butylamide | 700 |
| 20 | 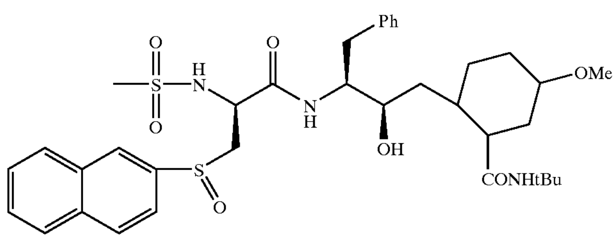 | 2-{2-Hydroxy-3-[2-methanesulfonylamino-3-(naphthalene-2-sulfinyl)-propionylamino]-4-phenyl-butyl}-5-methoxy-cyclohexanecarboxylic acid tert-butylamide | 700 |
| 21 | 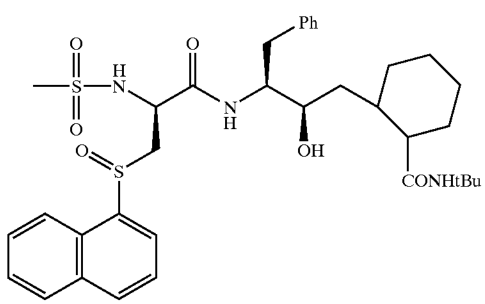 | 2-{2-Hydroxy-3-[2-methanesulfonylamino-3-(naphthalene-1-sulfinyl)-propionylamino]-4-phenyl-butyl}-cyclohexanecarboxylic acid tert-butylamide | 670 |

EXAMPLE 22

2-{2-Hydroxy-3-[2-methanesulfonylamino-3-(naphthalen-2-sulfonyl)-propionylaminol]-4-phenyl-butyl}-5-methoxy-cyclohexanecarboxylic Acid tert-Butylamide (Ex. 23)

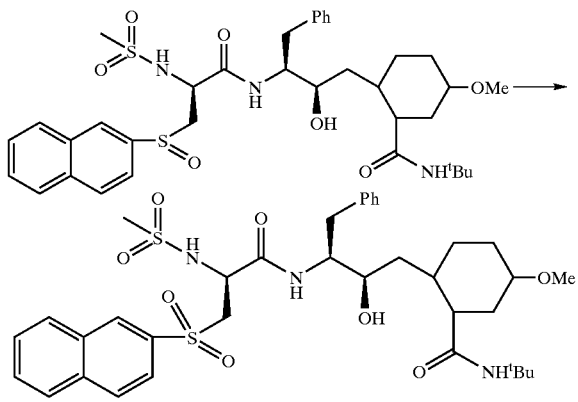

A solution of 2-{2-hydroxy-3-[2-methanesulfonylamino-3-(naphthalen-2-sulfinyl)-propionylamino]-4-phenyl-butyl}-5-methoxy-cyclohexanecarboxylic acid tert-butylamide in dichloromethane (2 ml) was treated with a solution of meta-chloroperbenzoic acid (13 mg) in dichloromethane (1 ml) and the reaction mixture stirred at room temperature for 2 hours. The solution was then washed with 5% aqueous sodium hydrogen carbonate solution, dried (anhydrous magnesium sulfate) and concentrated in vacuo to give 2-{2-hydroxy-3-[2-methanesulfonylamino-3-(naphthalen-2-sulfonyl)-propionylamino]-4-phenyl-butyl}-5-methoxy-cyclohexanecarboxylic acid tert-butylamide (23 mg, 92%) as a white foam. Mass spectrum, 717 $[M+H]^+$.

The following compounds have been prepared in a similar manner from the appropriate sulfoxide:

| Ex. | Structure | Name | $[M + H]^+$ |
|---|---|---|---|
| 23 | 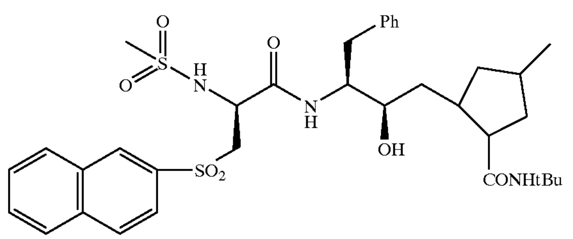 | 2-{2-Hydroxy-3-[2-methanesulfonylamino-3-(naphthalene-2-sulfonyl)-propionylamino]-4-phenyl-butyl}-4-methyl-cyclopentanecarboxylic acid tert-butylamide | 686 |
| 24 | 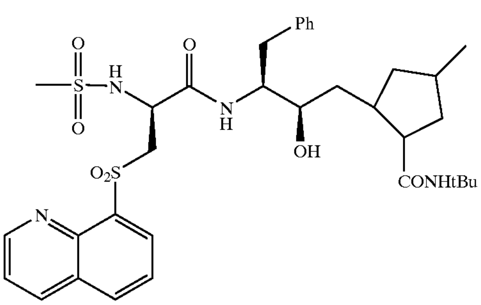 | 2-{2-Hydroxy-3-[2-methanesulfonylamino-3-(quinoline-8-sulfonyl)-propionylamino]-4-phenyl-butyl}-4-methyl-cyclopentanecarboxylic acid tert-butylamide | 687 |
| 25 | 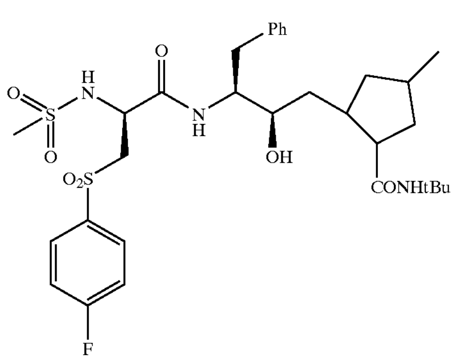 | 2-{3-[3-(4-Fluoro-benzenesulfonyl)-2-methanesulfonylamino-propionylamino]-2-hydroxy-4-phenyl-butyl}-4-methyl-cyclopentanecarboxylic acid tert-butylamide | 654 |

-continued

| Ex. | Structure | Name | [M + H]+ |
|---|---|---|---|
| 26 | 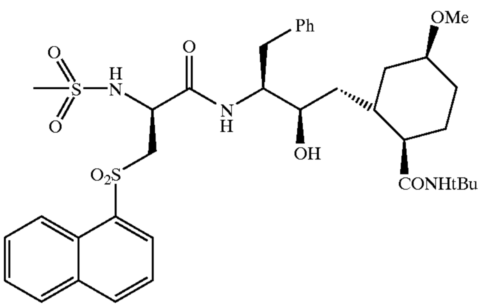 | 2-{2-Hydroxy-3-[2-methanesulfonylamino-3-(naphthalene-1-sulfonyl)-propionylamino]-4-phenyl-butyl}-4-methoxy-cyclohexanecarboxylic acid tert-butylamide | 716 |
| 27 | 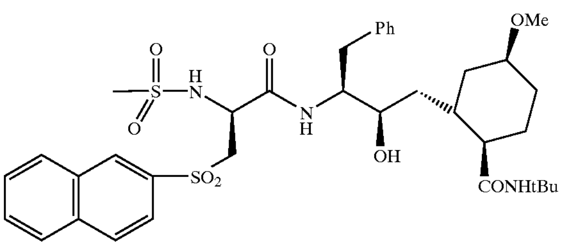 | N-tert-Butyl-2-[2-hydroxy-3-[[N2-(methanesulfonyl)-S-(2-naphthyl)-D-cysteinyl]amino]-4-phenylbutyl]-4-methoxy-1-cyclohexanecarboxamide S,S-dioxide | 716 |
| 28 | 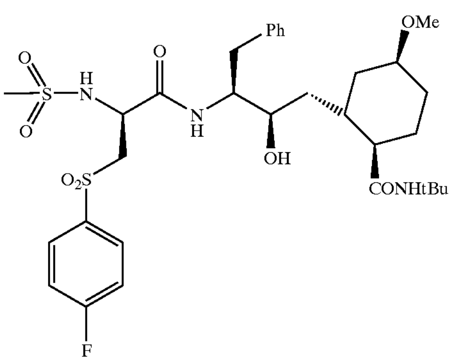 | 2-{3-[3-(4-Fluoro-benzenesulfonyl)-2-methane-sulfonylamino-propionylamino]-2-hydroxy-4-phenyl-butyl}-4-methoxy-cyclohexanecarboxylic acid tert-butylamide | 654 |
| 29 | 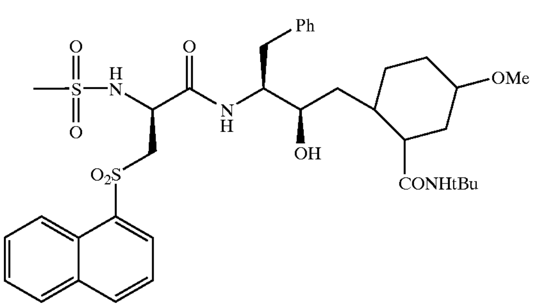 | 2-{2-Hydroxy-3-[2-methanesulfonylamino-3-(naphthalene-1-sulfonyl)-propionylamino]-4-phenyl-butyl}-5-methoxy-cyclohexanecarboxylic acid tert-butylamide | 716 |
| 30 | 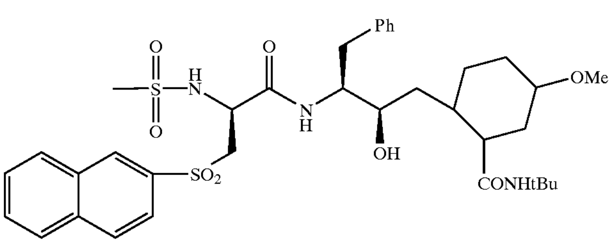 | 2-{2-Hydroxy-3-[2-methanesulfonylamino-3-(naphthalene-2-sulfonyl)-propionylamino]-4-phenyl-butyl}-5-methoxy-cyclohexanecarboxylic acid tert-butylamide | 716 |

-continued

| Ex. | Structure | Name | [M + H]+ |
|---|---|---|---|
| 31 | 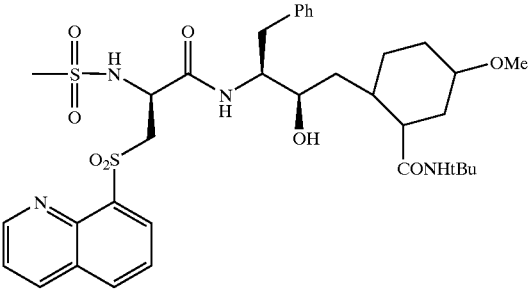 | 2-{2-Hydroxy-3-[2-methanesulfonylamino-3-(quinoline-8-sulfonyl)-propionylamino]-4-phenyl-butyl}-5-methoxy-cyclohexanecarboxylic acid tert-butylamide | 717 |
| 32 | 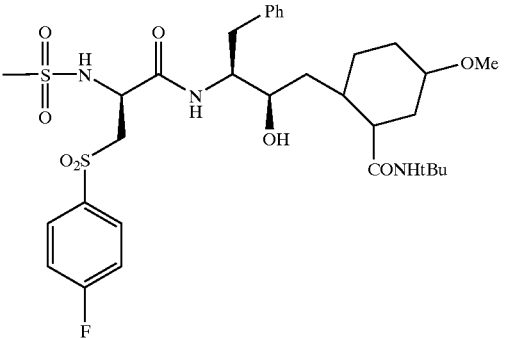 | 2-{3-[3-(4-Fluoro-benzenesulfonyl)-2-methane-sulfonylamino-propionylamino]-2-hydroxy-4-phenyl-butyl}-5-methoxy-cyclohexanecarboxylic acid tert-butylamide | 684 |
| 33 | 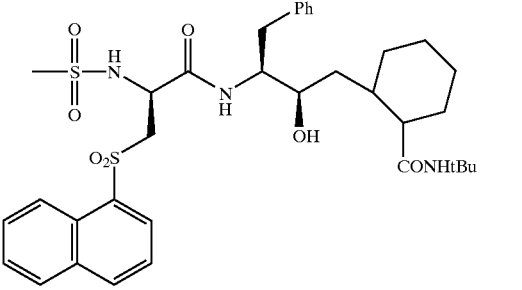 | 2-{2-Hydroxy-3-[2-methanesulfonylamino-3-(naphthalene-1-sulfonyl)-propionylamino]-4-phenyl-butyl}-cyclohexanecarboxylic acid tert-butylamide | 686 |

In manner analogous to that described for examples 26–28 the following compounds have been prepared:

| Ex. | Structure | name | [M + H]+ |
|---|---|---|---|
| 34 | 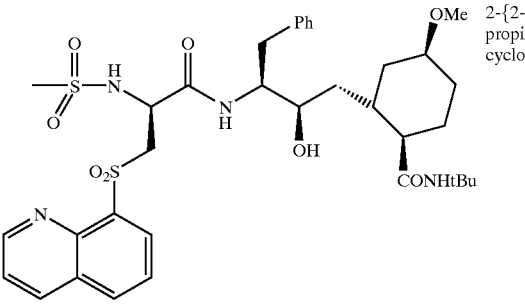 | 2-{2-Hydroxy-3-[2-methanesulfonylamino-3-(quinoline-8-sulfonyl)-propionylamino]-4-phenyl-butyl}-4-methoxy-cyclohexanecarboxylic acid tert-butylamide | 717 |

| Ex. | Structure | name | [M + H]+ |
|---|---|---|---|
| 35 | 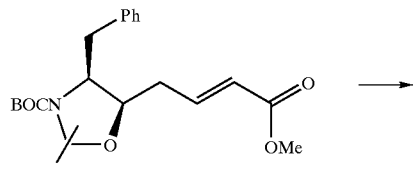 | 2-{2-Hydroxy-3-[2-methanesulfonylamino-3-(quinoline-2-sulfonyl)-propionylamino]-4-phenyl-butyl}-4-methoxy-cyclohexanecarboxylic acid tert-butylamide | 717 |

Scheme B 5-(2-Benzenesulfonyl-5-methoxycarbonyl-3-methylene-cyclopentylmethyl)-4-benzyl-2,2-dimethyl-oxazolidine-3-carboxylic Acid tert-Butyl Ester 5-(2-Benzenesulfonyl-5-methoxycarbonyl-3-methylene-cyclopent-2-enylmethyl)-4-benzyl-2,2-dimethyl-oxazolidine-3-carboxylic Acid tert-Butyl Ester

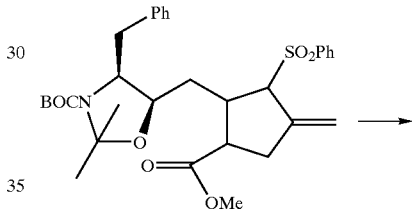

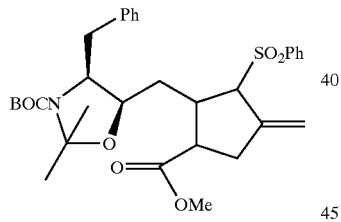

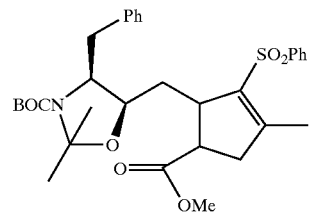

A solution of (2-Bromomethyl-prop-2-ene-1-sulfonyl)-benzene (25.4 g, 92.5 mmol) in dry tetrahydrofuran (500 ml) was stirred at −78° C. under nitrogen during the addition of lithium diisopropyl amide (2M in hexanes, 46.3 ml, 92.5 mmol). The resulting mixture was stirred at −78° C. for 15 minutes and 4-Benzyl-5-(3-methoxycarbonyl-allyl)-2,2-dimethyl-oxazolidine-3-carboxylic acid tert-butyl ester (30 g, 77 mmol) in dry tetrahydrofuran (150 ml) then added via a cannula over 5 minutes. The resulting mixture was stirred at −78° C. for 2 hours, then quenched with saturated aqueous ammonium chloride solution and warmed to room temperature. After addition of brine and ethyl acetate, the phases were separated and the aqueous layer extracted with ethyl acetate. The combined organic layers were washed with brine, dried (anhydrous magnesium sulfate) and concentrated in vacuo to give, after purification by flash chromatography on silica gel (ethylacetate/hexane: 1/9 to 4/6) 5-(2-Benzenesulfonyl-5-methoxycarbonyl-3-methylene-cyclopentylmethyl)-4-benzyl-2,2-dimethyl-oxazolidine-3-carboxylic acid tert-butyl ester 41 g (89%) as a white foam. Mass spectrum 584 [M+H]+.

A solution of 5-(2-Benzenesulfonyl-5-methoxycarbonyl-3-methylene-cyclopentylmethyl)-4-benzyl-2,2-dimethyl-oxazolidine-3-carboxylic acid tert-butyl ester (41 g, 68.7 mmol) in of dry methanol (150 ml) was stirred at 0° C. under nitrogen during the addition of (75.5 mmol, 1.1 equiv.) of sodium ethoxide (5.13 g, 75.5 mmol). The solution was stirred at 0° C. for 5 hours and than quenched with saturated aqueous ammonium chloride solution. After dilution with brine and ethyl acetate, the layers were separated and the aqueous phase was extracted twice with ethyl acetate. The combined organic layers were washed with brine and dried (anhydrous magnesium sulfate. The solvent was removed in vacuo to give crude 5-(2-Benzenesulfonyl-5-methoxycarbonyl-3-methylene-cyclopent-2-enylmethyl)-4-benzyl-2,2-dimethyl-oxazolidine-3-carboxylic acid tert-butyl ester (38 g, 92%) which was used in the next step without further purification.

4-Benzyl-5-(5-methoxycarbonyl-3-methyl-cyclopent-2-enylmethyl)-2,2-dimethyl-oxazolidine-3-carboxylic Acid tert-Butyl Ester

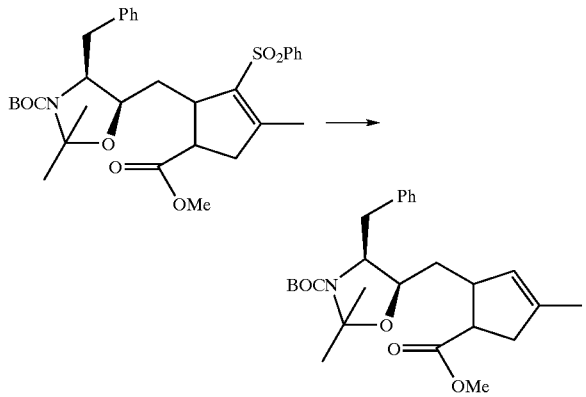

A solution of 5-(2-Benzenesulfonyl-5-methoxycarbonyl-3-methylene-cyclopent-2-enylmethyl)-4-benzyl-2,2-dimethyl-oxazolidine-3-carboxylic acid tert-butyl ester (33.55 g, 56.2 mmol) in dry methanol (250 ml) was stirred at −20° C. under nitrogen during the sequential addition of potassium dihydrogen orthophosphate (15 g, 11 mmol) and sodium mercury amalgam (32 g 10% w/w in sodium, mmol)). The vigorously stirred solution was allowed to warm to 0° C. and stirred at this temperature for 18 hours. The mercury was removed by filtration, and most of the solvent was removed in vacuo. The crude product was dissolved in ethyl acetate, and the solution washed with brine, dried (anhydrous magnesium sulfate). and concentrated in vacuo to give, after purification by flash chromatography on silica gel (ethylacetate/hexane: 1/9 to 1/3), 4-Benzyl-5-(5-methoxycarbonyl-3-methyl-cyclopent-2-enyl methyl)-2,2-dimethyl-oxazolidine-3-carboxylic acid tert-butyl ester (22.65 g, 91%). Mass spectrum 444 [M+H]⁺.

4-Benzyl-5-(5-carboxy-3-methyl-cyclopent-2-enylmethyl)-2,2-dimethyl-oxazolidine-3-carbocylic Acid tert-Butyl Ester

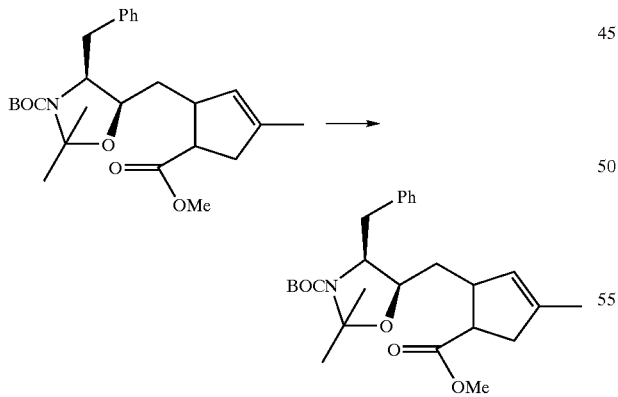

A solution of 4-Benzyl-5-(5-methoxycarbonyl-3-methyl-cyclopent-2-enylmethyl)-2,2-dimethyl-oxazolidine-3-carbocylic acid tert-butyl ester (1.25g, 2.73 mmol) in dry dioxane (15 ml) at 0° C. during the addition of 1M aqueous lithium hydroxide solution (5.5 ml, 5.5 mmol). The mixture was allowed to warm to room temperature and stirred for 25 hours. After removal of most of the dioxane in vacuo, the residue was dissolved in ethyl acetate and washed with a 1:1 mixture of brine and 1M hydrochloric acid. The acidic aqueous phase was extracted with ethyl acetate and the combined organic phases were dried (anhydrous magnesium sulfate) and concentrated in vacuo to provide 4-Benzyl-5-(5-carboxy-3-methyl-cyclopent-2-enylmethyl)-2,2-dimethyl-oxazolidine-3-carbocylic acid tert-butyl ester (1.24 g, 98%) as a yellow oil which was used in the next step without further purification.

4-Benzyl-5-(5-tert-butylcarbamoyl-3-methyl-cyclopent-2-enylmethyl)-2,2-dimethyl-oxazolidine-3-carbocylic Acid tert-Butyl Ester

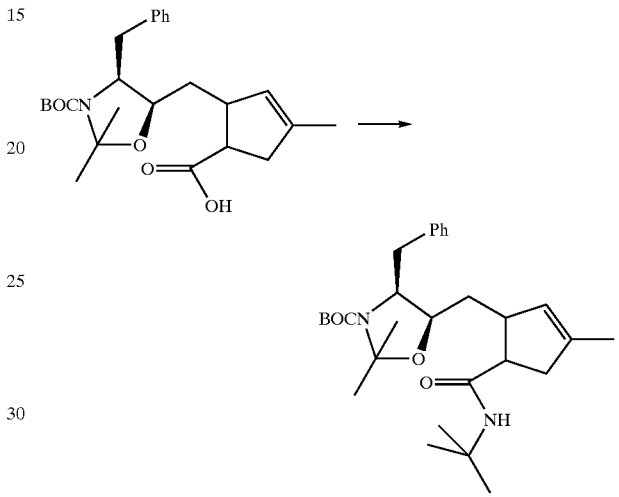

A solution of 4-Benzyl-5-(5-carboxy-3-methyl-cyclopent-2-enylmethyl)-2,2-dimethyl-oxazolidine-3-carbocylic acid tert-butyl ester (expected 2.73 mmol) in dry dichloromethane (30 ml) was stirred at 0° C. during the sequential addition of tert-butyl amine (860 μl, 8.2 mmol), 1-hydroxybenzotriazole hydrate (442 mg, 3.28 mmol) and N-ethyl-N'-(3-dimethylaminopropyl)carbodiimide hydrochloride (627 mg, 3.28 mmol). The mixture was allowed to warm to room temperature, stirred for 20 hours and concentrated in vacuo. The crude product was dissolved in ethyl acetate and the solution was washed with saturated aqueous sodium hydrogen carbonate solution, 1M hydrochloric acid and brine, dried (anhydrous magnesium sulfate) and concentrated in vacuo to give, after purification by flash chromatography on silica gel (ethyl acetate/hexane: 1/9 to 1/3), 4-benzyl-5-(5-tert-butylcarbamoyl-3-methyl-cyclopent-2-enylmethyl)-2,2-dimethyl-oxazolidine-3-carbocylic acid tert-butyl ester (1.01 g, 76%). Mass spectrum 485 [M+H]⁺.

4-Benzyl-5-(2-tert-butylcarbamoyl-4-methyl-cyclopentylmethyl)-2,2-dimethyl-oxazolidine-3-carbocylic Acid tert-Butyl Ester

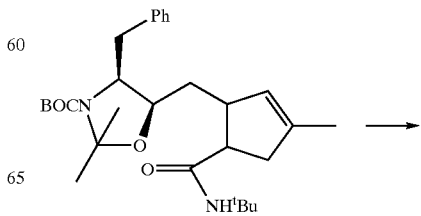

-continued

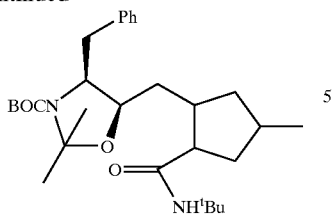

A solution of 4-benzyl-5-(5-tert-butylcarbamoyl-3-methyl-cyclopent-2-enylmethyl)-2,2-dimethyl-oxazolidine-3-carbocylic acid tert-butyl ester (500 mg, 1.03 mmol) in dry methanol (10 ml), was hydrogenated over 5% Pd on charcoal (50 mg) for 20 hours. After filtration of the catalyst, the mixture was concentrated in vacuo to give 4-benzyl-5-(2-tert-butylcarbamoyl-4-methyl-cyclopentylmethyl)-2,2-dimethyl-oxazolidine-3-carbocylic acid tert-butyl ester (472 mg, 94%) as a white foam which was used in the next step without further purification.

Scheme C (2-Methyl-prop-2-ene-1-sulfonyl)-benzene

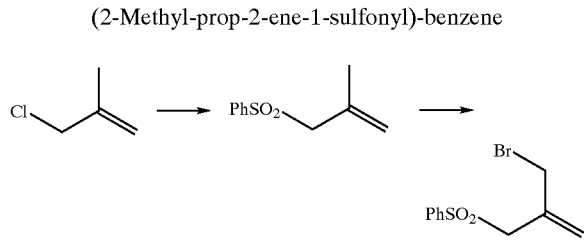

A solution of 3-chloro-2-methyl-propene (80 ml, 0.81 mmol) in dry methanol (450 ml) was stirred at room temperature during the addition of sodium benzenesulfinate (200 g, 1.22 mmol). The resulting suspension was refluxed for 20 hours, cooled to room temperature and concentrated in vacuo. The residue was poured onto water (600 ml) and the resulting solid filtered, washed three times with water (200 ml) and dried under vacuum for two days to give (2-methyl-prop-2-ene-1-sulfonyl)-benzene (156 g, 99%) which was used in the next step without further purification.

A solution of (2-methyl-prop-2-ene-1-sulfonyl)-benzene (156 g, 0.80 mmol) in dry dichloromethane (1 L) was stirred at room temperature under nitrogen during the dropwise addition of sulfuryl chloride (77 ml, 0.96 mmol). The resulting mixture was stirred at room temperature for 20 minutes and then refluxed for 45 min. After cooling to room temperature, the solution was concentrated in vacuo to give the allylic chloride as a white precipitate (186 g, 100%) which was used in the next step without further purification.

A solution of crude (2-chloromethyl-prop-2-ene-1-sulfonyl)-benzene (186 g, assumed 0.80 mmol) in a mixture of dibromomethane (400 ml) and of dimethylformamide (800 ml) was stirred at room temperature during the addition of sodium bromide (82 g, 0.80 mmol). The resulting suspension was stirred at 100° C. for 16 hours, then cooled to room temperature and concentrated in vacuo. The crude material was dissolved in of ethyl acetate (750 ml) and the resulting solution was washed with water (750 ml) and brine (750 ml), dried (anhydrous magnesium sulfate) and concentrated in vacuo. The crude product was recrystallised from isopropyl ether to give (2-bromomethyl-prop-2-ene-1-sulfonyl)-benzene (82 g, 37%). Mass spectrum 276 [M+H]$^+$.

Scheme D

4-Benzyl-5-(2-formyl-3-methoxycarbonyl-5-oxo-hexyl)-2,2-dimethyl-oxazolidine-3-carboxylic Acid tert-Butyl Ester

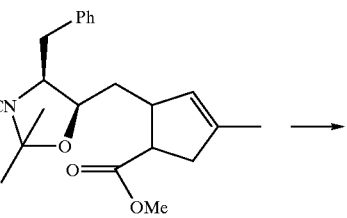

A stream of $O_3/O_2$ was passed through a solution of 4-benzyl-5-(5-methoxycarbonyl-3-methyl-cyclopent-2-enylmethyl)-2,2-dimethyl-oxazolidine-3-carboxylic acid tert-butyl ester (12 g, 27 mmol) in dry dichloromethane (200 ml) and dry methanol (50 ml) at −78° C. until the colour of the solution turned blue. After purging the resulting solution with oxygen, triphenylphosphine (9.9 g, 38 mmol) was added and the resulting mixture was allowed to warm to −30° C. over 1.5 h, then to room temperature over 2 hours. The solvent was removed in vacuo and the residue purified by flash chromatography on silica gel (ethyl acetate/hexane: 1/9 then 4/6) to give 4-benzyl-5-(2-formyl-3-methoxycarbonyl-5-oxo-hexyl)-2,2-dimethyl-oxazolidine-3-carboxylic acid tert-butyl ester (13.5 g, 100%). Mass spectrum 476 [M+H]$^+$.

4-Benzyl-5-(6-methoxycarbonyl-4-oxo-cyclohex-2-enylmethyl)-2,2-dimethyl-oxazolidine-3-carboxylic Acid tert-Butyl Ester

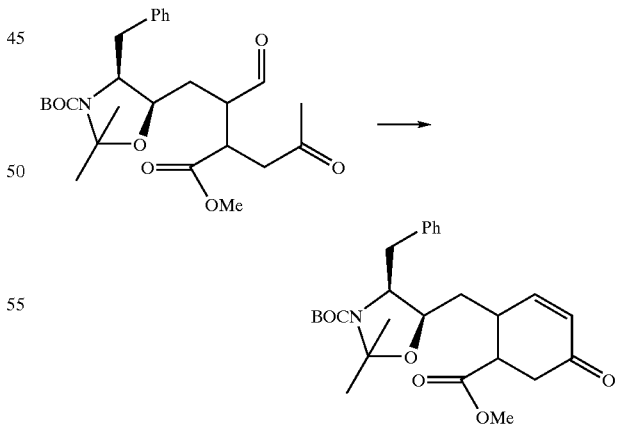

A solution of 4-benzyl-5-(2-formyl-3-methoxycarbonyl-5-oxo-hexyl)-2,2-dimethyl-oxazolidine-3-carboxylic acid tert-butyl ester (13.5 g, 27 mmol) and para-toluenesulfonic acid monohydrate (660 mg, 2.7 mmol) in dry toluene (250 ml), was refluxed for 24 hours using a Dean-Stark apparatus to remove water formed during the reaction. The mixture was then cooled to room temperature and treated with and saturated aqueous sodium hydrogen carbonate solution (20 ml). After dilution with ethyl acetate and brine, the layers were separated and the aqueous layer extracted with ethyl acetate. The combined organic layers were washed with brine, dried (anhydrous magnesium sulfate) and concentrated in vacuo. Purification by flash chromatography on silica gel provided 4-benzyl-5-(6-methoxycarbonyl-4-oxo-cyclohex-2-enylmethyl)-2,2-dimethyl-oxazolidine-3-carboxylic acid tert-butyl ester (5.64 g, 43%). Mass spectrum 458 [M+H]+.

4-Benzyl-5-(2-methoxycarbonyl-4-oxo-cyclohexylmethyl)-2,2-dimethyl-oxazolidine-3-carboxylic Acid tert-Butyl Ester

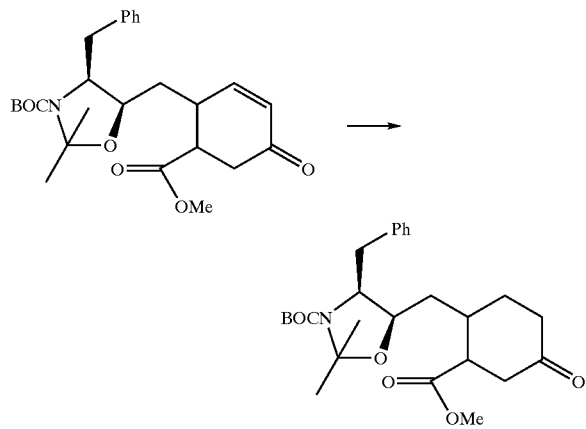

A solution of 4-benzyl-5-(6-methoxycarbonyl-4-oxo-cyclohex-2-enylmethyl)-2,2-dimethyl-oxazolidine-3-carboxylic acid tert-butyl ester (6 g, 13,1 mmol) in ethyl acetate (30 ml) was hydrogenated over 5% Pd on charcoal (600 mg for 2 hours. The catalyst was removed by filtration through Hyflo and the solvent removed in vacuo to give 4-benzyl-5-(2-methoxycarbonyl-4-oxo-cyclohexylmethyl)-2,2-dimethyl-oxazolidine-3-carboxylic acid tert-butyl ester (6 g, 100%), which was used in the next step without further purification.

4-Benzyl-5-(2-carboxy-4-oxo-cyclohexylmethyl)-2,2-dimethyl-oxazolidine-3-carboxylic Acid tert-Butyl Ester

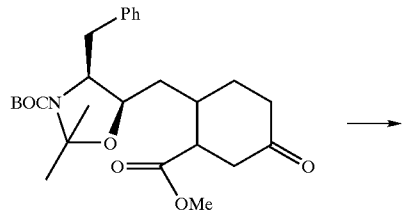

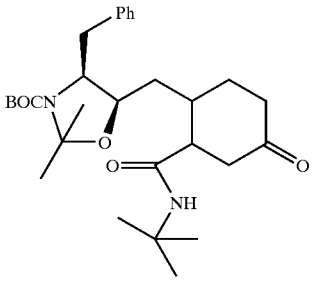

A solution of 4-benzyl-5-(2-methoxycarbonyl-4-oxo-cyclohexylmethyl)-2,2-dimethyl-oxazolidine-3-carboxylic acid tert-butyl ester (1.81 g, 3.94 mmol) in dry tetrahydrofuran (24 ml) was treated with 1M aqueous lithium hydroxide solution (8 ml 7.88 mM). The resulting mixture was stirred at room temperature for 6 hours then diluted with ethyl acetate, washed with a 1:1 mixture of brine and 1 M hydrochloric acid, dried (anhydrous magnesium sulfate) and concentrated in vacuo to give 4-benzyl-5-(2-carboxy-4-oxo-cyclohexylmethyl)-2,2-dimethyl-oxazolidine-3-carboxylic acid tert-butyl ester (1.66 g, 95%) as a yellow oil which was used in the next step without further purification.

A solution of 4-Benzyl-5-(2-carboxy-4-oxo-cyclohexylmethyl)-2,2-dimethyl-oxazolidine-3-carboxylic acid tert-butyl ester (1.66 g, 3.74 mmol) in dry dichloromethane (20 ml) was stirred at 0° C. during sequential treatment with tert-butyl amine (1.4 ml, 12.7 mmol), 1-hydroxybenzotriazole hydrate (570 mg, 5 mmol) and N-ethyl-N'-(3-dimethylaminopropyl)carbodiimide hydrochloride (970 mg, 5 mmol). The resulting mixture was allowed to warm to room temperature and was stirred for 20 hours and then concentrated in vacuo. The crude mixture was dissolved in ethyl acetate and the resulting solution washed with saturated aqueous sodium hydrogen carbonate solution, 1 M hydrochloric acid and brine, dried (anhydrous magnesium sulfate) and concentrated in vacuo. Purification by flash chromatography on silica gel (ethyl acetate/hexane: 1/3 to 4/6) provided 4-benzyl-5-(2-tert-butylcarbamoyl-4-oxo-cyclohexylmethyl)-2,2-dimethyl-oxazolidine-3-carboxylic acid tert-butyl ester (1.2 g, 61%). Mass spectrum 502 [M+H]+.

4-Benzyl-5-(2-tert-butylcarbamoyl-4-hydroxy-cyclohexylmethyl)-2,2-dimethyl-oxazolidine-3-carboxylic Acid tert-Butyl Ester

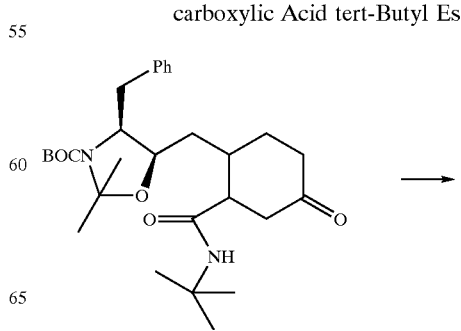

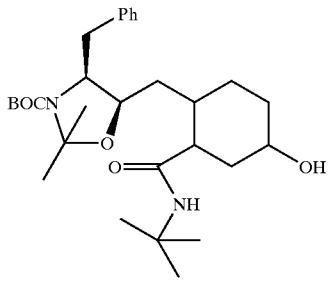

A solution of 4-benzyl-5-(2-tert-butylcarbamoyl-4-oxo-cyclohexylmethyl)-2,2-dimethyl-oxazolidine-3-carboxylic acid tert-butyl ester (1.1 g, 2.2 mmol) in dry methanol (20 ml) was stirred at room temperature under nitrogen during the addition of cerium chloride (1.8 g, 4.84 mmol). The resulting mixture was stirred at room temperature for 30 minutes, then cooled to −78° C. and treated with sodium borohydride (183 mg, 4.84 mmol). The resulting suspension was allowed to warm to 0° C. over 90 min, then partitioned between ethyl acetate and a mixture of saturated aqueous ammonium chloride solution and brine. The two layers were separated and the aqueous phase was extracted twice with ethyl acetate. The combined organic layers were dried (anhydrous magnesium sulfate) and concentrated in vacuo. Purification by flash chromatography on silica gel (ethyl acetate/hexane: 1/1 to 2/1) provided 4-benzyl-5-(2-tert-butylcarbamoyl-4-hydroxy-cyclohexylmethyl)-2,2-dimethyl-oxazolidine-3-carboxylic acid tert-butyl ester (860 mg).

4-Benzyl-5-(2-tert-butylcarbamoyl-4-hydroxy-cyclohexylmethyl)-2,2-dimethyl-oxazolidine-3-carboxylic Acid tert-Butyl Ester

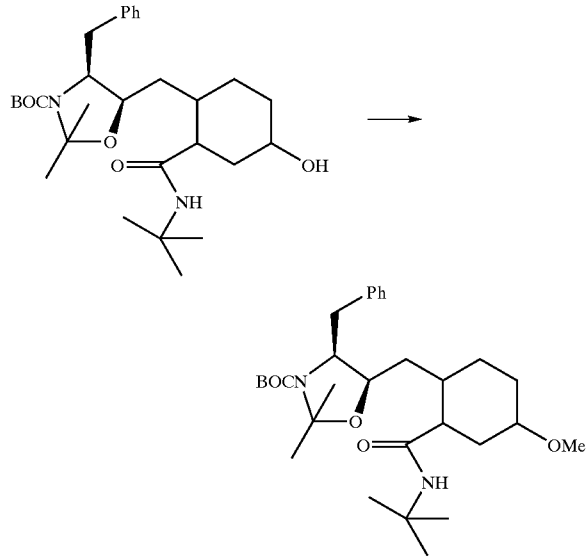

Sodium hydride (60% dispersion in mineral oil, 116 mg, 2.9 mmol) was added to a solution of 4-benzyl-5-(2-tert-butylcarbamoyl-4-hydroxy-cyclohexylmethyl)-2,2-dimethyl-oxazolidine-3-carboxylic acid tert-butyl ester (730 mg, 1.45 mmol in dry N,N-dimethylformamide (14 ml) stirred at 0° C. under nitrogen The resulting mixture was stirred at this temperature for 90 min, cooled to 0° C. and methyl iodide (133 μl, 2.17 mmol) was added. The resulting mixture was allowed to warm to room temperature over 12 hours then concentrated in vacuo and dissolved in ethyl acetate. The organic phase was washed with water and brine, dried (anhydrous magnesium sulfate) and concentrated in vacuo. Purification by flash chromatography on silica gel (ethyl acetate/hexane: 3/7) provided 4-benzyl-5-(2-tert-butylcarbamoyl-4-hydroxy-cyclohexylmethyl)-2,2-dimethyl-oxazolidine-3-carboxylic acid tert-butyl ester (530 mg, 73%) as a white foam.

Scheme E

4-Benzyl-5-[2-(-4-benzyl-2-oxo-oxazolidine-3-carbonyl)-5-oxo-cyclohexylmethyl]-2,2-dimethyl-oxazolidine-3-carboxylic Acid tert-Butyl Ester

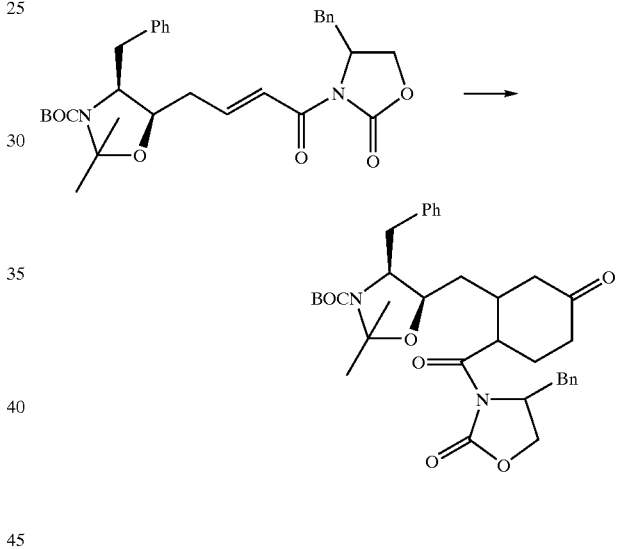

A solution of 4-Benzyl-5-[4-(-4-benzyl-2-oxo-oxazolidin-3-yl)-4-oxo-but-2-enyl]-2,2-dimethyl-oxazolidine-3-carboxylic acid tert-butyl ester (13.35 g, 25 mmol) in dichloromethane (500 ml) was stirred at −78° C. under nitrogen during the addition of 2-trimethylsiloxy-1,3-butadiene (26 ml, 150 mmol) and 1.8 M diethylaluminium chloride solution in toluene (70 ml, 125 mmol). The resulting pale yellow solution was stirred at −78° C. for 48 hours then slowly added to vigorously stirred, ice-cold 1 M hydrogen chloride aqueous solution. After 1 hour the two layers were separated and the aqueous phase was extracted twice with ethyl acetate. The combined organic layers were washed with a saturated aqueous sodium hydrogen carbonate solution and brine, dried (anhydrous magnesium sulfate) and concentrated in vacuo to give, after purification by flash chromatography on silica gel (ethyl acetate/hexane 1/9 to 4/6), 4-Benzyl-5-[2-(4-benzyl-2-oxo-oxazolidine-3-carbonyl)-5-oxo-cyclohexylmethyl]-2,2-dimethyl-oxazolidine-3-carboxylic acid tert-butyl ester (8.7 g) as a white foam.

4-benzyl-5-(2-carboxy-5-oxo-cyclohexylmethyl)-2,2-dimethyl-oxazolidine-3-carbocylic Acid tert-Butyl Ester

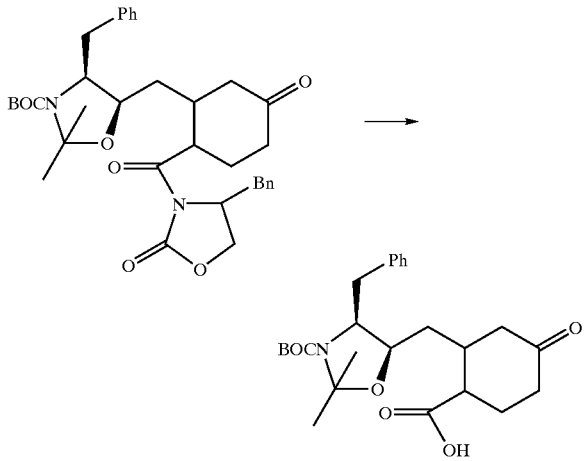

A solution of 4-benzyl-5-[2-(4-benzyl-2-oxo-oxazolidine-3-carbonyl)-5-oxo-cyclohexylmethyl]-2,2-dimethyl-oxazolidine-3-carboxylic acid tert-butyl ester (1.65 g, 2.7 mmol) in tetrahydrofuran (40 ml) and water (13 ml) was stirred at 0° C. during the addition of 30% w/w aqueous hydrogen peroxide (1.25 ml, 10.9 mmol) and lithium hydroxide (229 mg 5.46 mmol). The resulting mixture was stirred at 0° C. for 1.5 hours, and then 1.5 N aqueous sodium sulfite solution (8 ml, 12 mmol) was added. The reaction mixture was stirred for another 30 min and then partitioned between ethyl acetate and 1M aqueous hydrogen chloride solution. The acidic aqueous layer was extracted with ethyl acetate and the combined organic layers were dried (anhydrous magnesium sulfate) and concentrated in vacuo to provide crude 4-benzyl-5-(2-carboxy-5-oxo-cyclohexylmethyl)-2,2-dimethyl-oxazolidine-3-carbocylic acid tert-butyl ester which was used in the next step without any further purification.

4-Benzyl-5-(2-tert-butylcarbamoyl-4-oxo-cyclohexylmethyl)-2,2-dimethyl-oxazolidine-3-carboxylic Acid tert-Butyl Ester

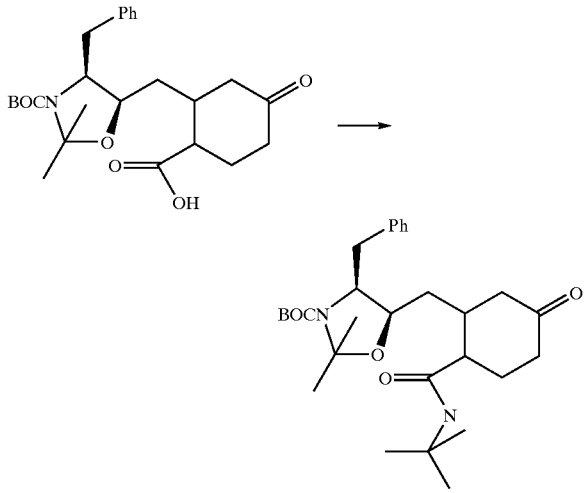

A solution of 4-benzyl-5-(2-carboxy-5-oxo-cyclohexylmethyl)-2,2-dimethyl-oxazolidine-3-carbocylic acid tert-butyl ester (g, expected 2.7 mmol) in dry dichloromethane (25 ml) was stirred at 0° C. during the sequential addition of tert-butyl amine (700 µl, 6.5 mmol), 1-hydroxybenzotriazole hydrate (400 mg, 3 mmol) and N-ethyl-N'-(3-dimethylaminopropyl)carbodiimide hydrochloride (570 mg, 3 mmol, 1.1 equiv.). The resulting mixture was allowed to warm to room temperature, stirred for 20 hours and then concentrated in vacuo. The crude mixture was dissolved in ethyl acetate and the resulting solution washed sequentially with saturated aqueous sodium hydrogen carbonate solution, 1M aqueous hydrogen chloride solution and brine, dried (anhydrous magnesium sulfate) and concentrated in vacuo. Purification by flash chromatography on silica gel (ethyl acetate/hexane: 1/3 to 4/6) provided of 4-benzyl-5-(2-tert-butylcarbamoyl-4-oxo-cyclohexylmethyl)-2,2-dimethyl-oxazolidine-3-carboxylic acid tert-butyl ester (750 mg, 55%) as a white foam.

4-Benzyl-5-(2-tert-butylcarbamoyl-5-hydroxy-cyclohexylmethyl)-2,2-dimethyl-oxazolidine-3-carboxylic Acid tert-Butyl Ester

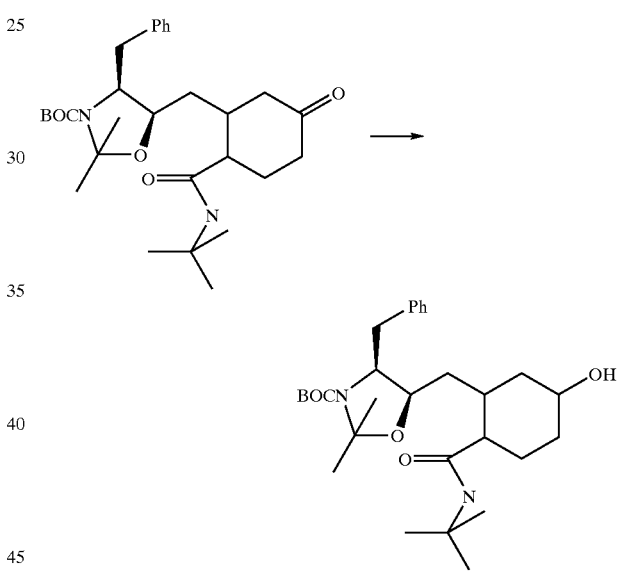

A solution of 4-benzyl-5-(2-tert-butylcarbamoyl-5-oxo-cyclohexylmethyl)-2,2-dimethyl-oxazolidine-3-carboxylic acid tert-butyl ester (980 mg, 1.96 mmol) in dry tetrahydrofuran was stirred at −78° C. under nitrogen during the addition of 1 M L-selectride solution in tetrahydrofuran (2.5 ml, 2.5 mmol). The resulting mixture was stirred at −78° C. for 30 minutes and then quenched by the addition of saturated aqueous ammonium chloride solution and allowed to warm to room temperature. The layers were separated and the aqueous phase was extracted with ethyl acetate. The combined organic phases were washed with 2N aqueous hydrogen chloride solution and brine, dried (anhydrous magnesium sulfate) and concentrated in vacuo. Purification by flash chromatography on silica gel (ethyl acetate/hexane: 7/3 to 1/0) provided of 4-benzyl-5-(2-tert-butylcarbamoyl-5-hydroxy-cyclohexylmethyl)-2,2-dimethyl-oxazolidine-3-carboxylic acid tert-butyl ester (934 mg, 95%) as a white foam.

4-Benzyl-5-(2-tert-butylcarbamoyl-5-methoxy-cyclohexylmethyl)-2,2-dimethyl-oxazolidine-3-carboxylic Acid tert-Butyl Ester

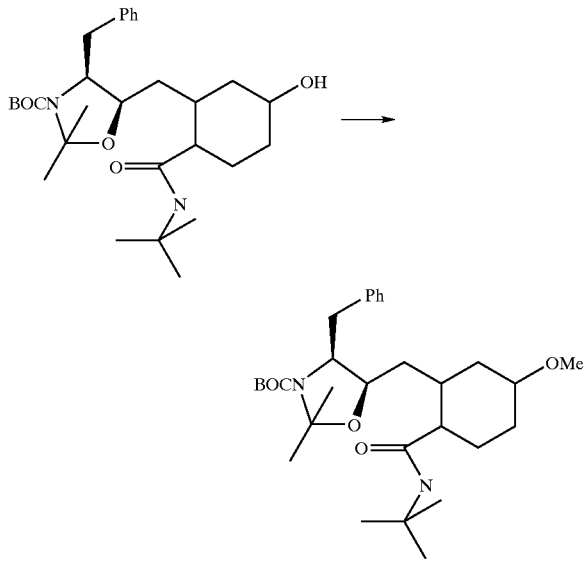

Sodium hydride (60% w/w in mineral oil, 20 mg, 0.52 mmol) was added to a solution of 4-benzyl-5-(2-tert-butylcarbamoyl-5-hydroxy-cyclohexylmethyl)-2,2-dimethyl-oxazolidine-3-carboxylic acid tert-butyl ester (200 mg, 0.40 mmol) in dry N,N-dimethylformamid (4 ml) stirred at 0° C. under nitrogen. The resulting mixture was stirred at 0° C. until gas evolution had ceased. Methyl iodide (40 µl, 0.6 mmol) was then added, and the solution was allowed to warm to room temperature and stirred for 20 hours. After removal of the volatiles in vacuo, the crude product was dissolved in ethyl acetate, washed twice with water, dried (anhydrous magnesium sulfate) and concentrated in vacuo. Purification by flash chromatography on silica gel provided 4-benzyl-5-(2-tert-butylcarbamoyl-5-methoxy-cyclohexylmethyl)-2,2-dimethyl-oxazolidine-3-carboxylic acid tert-butyl ester (125 mg, 96%).

Scheme F

4-Benzyl-5-(6-ethoxycarbonyl-cyclohex-3-enylmethyl)-2,2-dimethyl-oxazolidine-3-carboxylic Acid tert-Butyl Ester

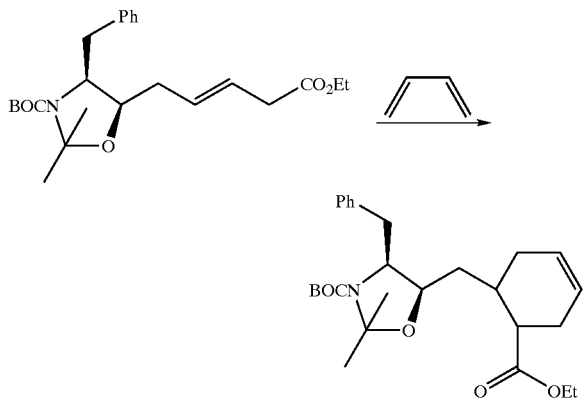

A solution of 4-benzyl-5-(3-ethoxycarbonyl-allyl)-2,2-dimethyl-oxazolidine-3-carboxylic acid tert-butyl ester (6.55 g) in toluene (50 ml) was placed in a stainless steel bomb equipped with a PTFE liner. Hydroquinone (350 mg) was added, and the vessel cooled to −78° C. 1,3-butadiene (100 g) was condensed into the vessel, which was then sealed and heated to 150° C. for 16 hours. After cooling, the vessel was opened and the contents removed and evaporated to dryness. The residue was subjected to flash chromatography on silica gel eluting with hexane/ethyl acetate (95:5) to afford 4-benzyl-5-(6-ethoxycarbonyl-cyclohex-3-enylmethyl)-2,2-dimethyl-oxazolidine-3-carboxylic acid tert-butyl ester (2.54 g, 34%) as a mixture of trans isomers (mass spectrum 458 [M+H]$^+$) together with recovered starting material (2.17 g, 33%).

4-Benzyl-5-(6-carboxy-cyclohex-3-enylmethyl)-2,2-dimethyl-oxazolidine-3-carboxylic Acid tert-Butyl Ester

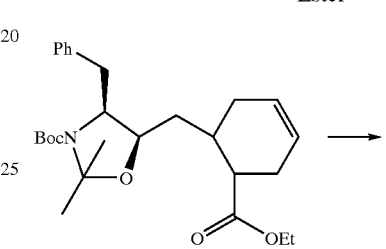

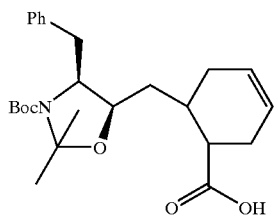

A solution of 4-benzyl-5-(6-ethoxycarbonyl-cyclohex-3-enylmethyl)-2,2-dimethyl-oxazolidine-3-carboxylic acid tert-butyl ester (4.72 g) in ethanol (80 ml) was treated with a solution of sodium hydroxide (0.82 g) in water (15 ml) and the resulting solution refluxed for 18 hours. The ethanol was then evaporated and the residue partitioned between water and ethyl acetate. The organic solution was washed with saturated sodium chloride solution, dried (anhydrous magnesium sulfate) and evaporated. The residue was subjected to flash chromatography on silica gel eluting with hexane/ethyl acetate (2:1) to afford 4-benzyl-5-(6-carboxy-cyclohex-3-enylmethyl)-2,2-dimethyl-oxazolidine-3-carboxylic acid tert-butyl ester (3.32 g, 75%) Mass spectrum 430 [M+H]$^+$.

4-Benzyl-5-(6-tert-butylcarbamoyl-cyclohex-3-enylmethyl)-2,2-dimethyl-oxazolidine-3-carboxylic Acid tert-Butyl Ester

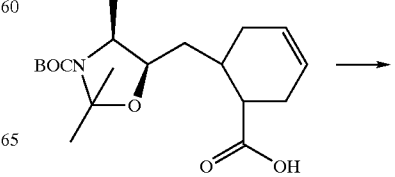

-continued

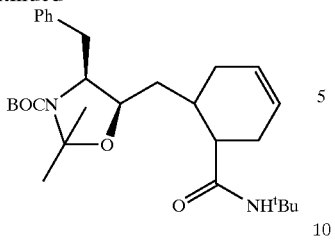

Scheme G

4-tert-Butoxycarbonylamino-3-oxo-5-phenyl-pentanoic Acid Ethyl Ester

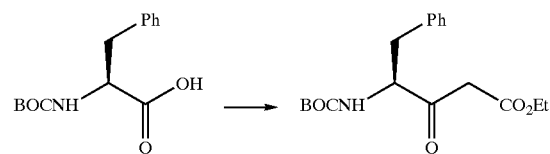

An ice-cooled, stirred solution of 4-benzyl-5-(6-carboxy-cyclohex-3-enylmethyl)-2,2-dimethyl-oxazolidine-3-carboxylic acid tert-butyl ester (3.0 g) in dichloromethane (70 ml) was treated with 1-(3-dimethylaminopropyl)-3-ethylcarbodiimide hydrochloide (1.61 g), 1-hydroxybenzotriazole and tert-butylamine (1.12 g). The reaction mixture was allowed to stir and warm to ambient temperature during 16 hours. The reaction mixture was then washed sequentially with 2M aqueous hydrochloric acid, 10% aqueous sodium bicarbonate solution, water and saturated aqueous sodium chloride solution, dried (anhydrous magnesium sulfate) and evaporated to give 4-benzyl-5-(6-tert-butylcarbamoyl-cyclohex-3-enylmethyl)-2,2-dimethyl-oxazolidine-3-carboxylic acid tert-butyl ester (322 g, 95%)

4-Benzyl-5-(2-tert-butylcarbamoyl-cyclohexylmethyl)-2,2-dimethyl-oxazolidine-3-carboxylic Acid tert-Butyl Ester

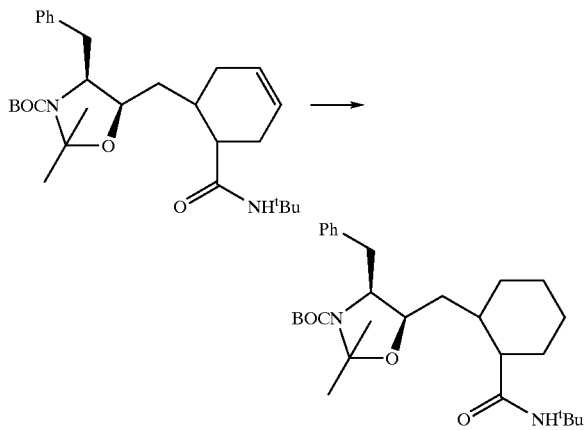

A solution of 4-benzyl-5-(6-tert-butylcarbamoyl-cyclohex-3-enylmethyl)-2,2-dimethyl-oxazolidine-3-carboxylic acid tert-butyl ester (100 mg) in ethanol (20 ml) was hydrogenated over 10% palladium on carbon for 3 hours at atmospheric pressure and ambient temperature. The catalyst was removed by filtration and the filtrate evaporated to give 4-benzyl-5-(2-tert-butylcarbamoyl-cyclohexylmethyl)-2,2-dimethyl-oxazolidine-3-carboxylic acid tert-butyl ester (100 mg, 100%) Mass spectrum 487 [M+H]$^+$.

A solution of BOC-phenylalaanine (100 g, 0.377 mol) in dry tetrahydrofuran (750 ml) was mechanically stirred at 0° C. under nitrogen during the portiowise addition of N,N'-carbonyldiimidazole (73 g, 0.453 mol). The internal temperature was maintained below 5° C. throughout the addition. After the addition was complete, the mixture was stirred for 4 hours at room temperature.

Mono-ethyl malonate (74 g, 0.566 mol) in dry tetrahydrofuran (500 ml) was stirred under nitrogen during the dropwise addition of isopropyl magnesium chloride (560 ml, 1.132 mol) over 2 hours, keeping the internal temperature between 5° C. to 10° C. After the addition was complete, the mixture was gradually heated to 50° C. (effervescence was observed). The mixture was stirred at 50° C. for 30 min (whereby effervescence has ceased), then cooled to 20° C. using an ice/water bath. The solution was then added dropwise to the mechanically stirred BOC-phenylalanine/N,N'-carbonyldiimidazole mixture under nitrogen over 30 minutes, maintaining the internal temperature below 5° C. The mixture was allowed to warm to room temperature and stirred for a further 16 hours. The reaction mixture was then poured onto ice-cold aqueous hydrogen chloride solution (863 ml of concentrated hydrogen chloride in 4 l of ice/water). The organic solution was washed sequentially with water (2 L), 5% aqueous sodium hydrogen carbonate solution, water (1 L) and brine (1 L), dried (anhydrous magnesium sulfate), filtered and evaporated. Drying under vacuum at 40° C. provided of 4-tert-butoxycarbonylamino-3-oxo-5-phenyl-pentanoic acid ethyl ester (115 g) which was used in the next step without further purification.

4-tert-Butoxycarbonylamino-3-hydroxy-5-phenyl-pentanoic Acid Ethyl Ester

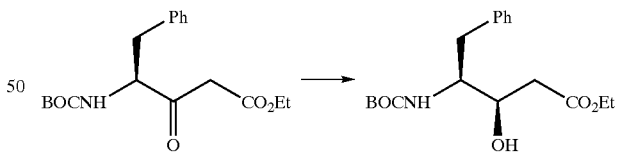

A mechanically stirred solution of 4-tert-butoxycarbonylamino-3-oxo-5-phenyl-pentanoic acid ethyl ester (115 g, 0.343 mol) in ethanol (450 ml) at 0° C. under nitrogen was treated portionwise with sodium borohydride (4.43 g, 0,117 mol) over 30 minutes, producing a thick slurry. The reaction mixture was quenched by the dropwise addition of glacial acetic acid (26 ml) at 0° C. under nitrogen. The slurry was then poured onto a mixture of dichloromethane (400 ml) and a 1M aqueous hydrogen chloride solution (400 ml) in a separating funnel. The organic layer was removed and the aqueous solution extracted with dichloromethane (180 ml). The combined organic solutions were washed sequentially with water (200 ml), 5% aqueous sodium hydrogen carbonate solution (200 ml) and brine (200 ml, and dried (anhydrous magnesium sulfate). The solvents were removed in vacuo to give an off-white solid which was recrystallised from methylcyclohexane/ethyl acetate providing 4-tert-butoxycarbonylamino-3-hydroxy-5-phenyl-pentanoic acid ethyl ester (77 g, 66%).

4-Benzyl-5-ethoxycarbonylmethyl-2,2-dimethyl-oxazolidone-3-carboxylic Acid tert-Butyl Ester

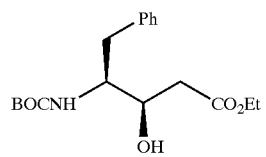 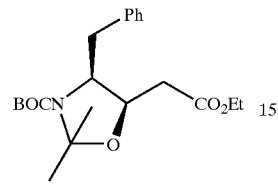

A mixture of 4-tert-butoxycarbonylamino-3-hydroxy-5-phenyl-pentanoic acid ethyl ester (77 g, 0.228 mol), 2,2-dimethoxypropane (500 ml, 4.07 mol), tetrahydrofuran (160 ml) and para-toluenesulfonic acid monohydrate (1.3 g) was heated with mechanical stirring to 55° C. for 19 h. The reaction mixture was allowed to cool to room temperature, diluted with diethyl ether (500 ml) and washed with 5% sodium hydrogen carbonate aqueous solution (500 ml) and brine (500 ml). The organic phase was dried (anhydrous magnesium sulfate), filtered and concentrated in vacuo to give 4-benzyl-5-ethoxycarbonylmethyl-2,2-dimethyl-oxazolidone-3-carboxylic acid tert-butyl ester (83.45 g, 97%) as a white solid.

4-Benzyl-2,2-dimethyl-(2-oxo-ethyl)-oxazolidine-3-carboxylic Acid tert-Butyl Ester

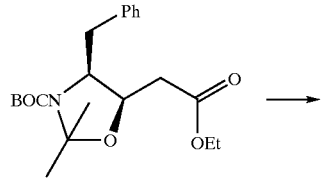

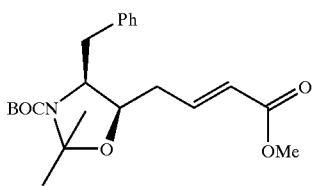

A solution of 4-benzyl-5-ethoxycarbonylmethyl-2,2-dimethyl-oxazolidine-3-carboxylic acid tert-butyl ester (48 g, 0.12 mol) in dry toluene was stirred at −78° C. during the addition of 1M diisobutyl aluminium hydride in toluene (165 ml, 165 mmol). The resulting mixture was stirred at −78° C. for 4 hours and ethyl acetate (60 ml) was then added. After 30 minutes, the mixture was allowed to warm to room temperature and a solution of potassium sodium L-tartrate tetrahydrate (250 g, mmoL) in water (800 ml) was added. The resulting biphasic mixture was stirred until the two phases were clear. The layers were separated and the aqueous layer was extracted with ethyl acetate. The combined organic layers were dried (anhydrous magnesium sulfate) and concentrated in vacuo to provide 4-benzyl-2,2-dimethyl-(2-oxo-ethyl)-oxazolidine-3-carboxylic acid tert-butyl ester which solidified upon standing overnight.

The white solid was dissolved in dry THF (600 ml) and treated with carboxymethylene triphenylphosphorane (53 g, 0.153 mol). The resulting mixture was stirred at room temperature for 12 hours and concentrated in vacuo to give, after purification by flash chromatography on silica gel (ethyl acetate/hexane: 1/4), 4-benzyl-5-(3-methoxycarbonyl-allyl)-2,2-dimethyl-oxazolidine-3-carboxylic acid tert-butyl ester (49 g, 100%).

4-Benzyl-5-(3-ethoxycarbonyl-2-oxo-propyl)-2,2-dimethyl-oxazolidine-3-carboxylic Acid tert-Butyl Ester

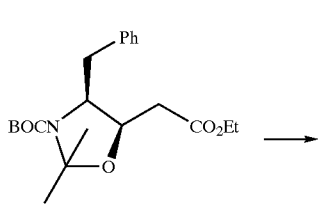

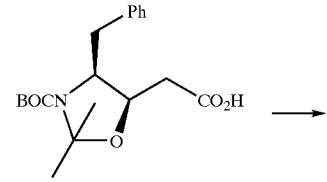

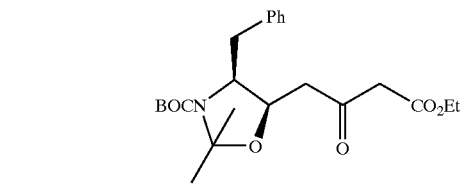

A suspension of 4-benzyl-5-ethoxycarbonylmethyl-2,2-dimethyl-oxazolidine-3-carboxylic acid tert-butyl ester (85.3 g) in ethanol (430 ml) was treated with a solution of sodium hydroxide (10.85 g) in water (45 ml) and the mixture stirred at ambient temperature for 3 hours. Most of the ethanol was removed by evaporation and the residue diluted with water (500 ml). The aqueous solution was washed with diethyl ether (2×250 ml), acidified to pH 1 using concentrated hydrochloric acid and then extracted with diethyl ether (500 ml and 250 ml). The second ether extracts were combined, washed with water, dried (anhydrous magnesium sulfate) and evaporated to give a white solid.

The solid was dissolved in anhydrous tetrahydrofuran (430 ml), the solution cooled to 0° C. under an atmosphere of nitogen and mechanically stirred during the portion-wise addition of 1,1-carbonyldiimidazole (44 g), maintaining the temperature below 5° C. After stirring for 1 hour, the suspension was treated dropwise with the magnesium enolate of mono-ethyl malonate prepared as described below, maintaining the temperature below 5° C. The mixture was allowed to warm to ambient temperature and stirred for 16 hours. The reaction mixture was then poured onto 2M aqueous hydrochloric acid (1.4 L) and extracted with diethyl ether (1.5 L and 1 L). The combined ether extracts were washed sequentially with water (700 ml), 5% aqueous sodium bicarbonate solution (700 ml), water (700 ml) and saturated aqueous sodium chloride solution (700 ml), dried (anhydrous magnesium sulfate) and evaporated. The residual oil was purified by flash chromatography on silica gel eluting with ethyl acetate/hexane (9:1) to give 4-benzyl-5-(3-ethoxycarbonyl-2-oxo-propyl)-2,2-dimethyl-oxazolidine-3-carboxylic acid tert-butyl ester (59.8 g, 63%) Mass spectrum 420 [M+H]⁺.

A stirred solution of mono-ethyl malonate (44.8 g) in anhydrous tetrahydrofuran was cooled to 0° C. under an atmosphere of nitrogen and treated dropwise with 2M isopropyl magnesium chloride in tetrahydrofuran (340 ml), maintaining the temperature between 0° C. and 5° C. throughout. The mixture was then heated slowly to 50° C., maintained at that temperature for 30 minutes and then cooled.

4-Benzyl-5-(3-ethoxycarbonyl-2-hydroxy-propyl)-2, 2-dimethyl-oxazolidine-3-carboxylic Acid tert-Butyl Ester

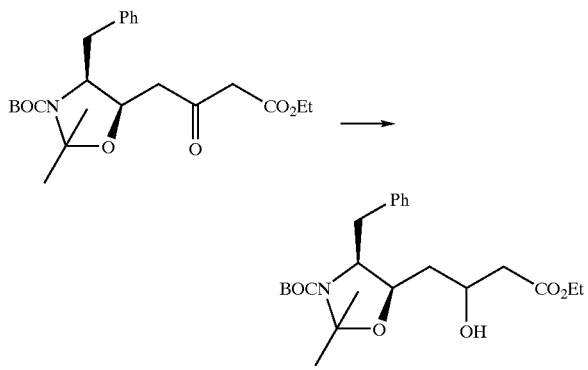

A solution of 4-benzyl-5-(3-ethoxycarbonyl-2-oxo-propyl)-2,2-dimethyl-oxazolidine-3-carboxylic acid tert-butyl ester (10 g) in ethanol (100 ml) was stirred at 15° C. under an atmosphere of nitrogen during the portion-wise addition of sodium borohydride (450 mg). The solution was stirred for a further 30 minutes, treated with glacial acetic acid (2 ml) and evaporated. The residue was partitioned between diethyl ether (200 ml) and 2M aqueous hydrochloric acid (100 ml). The organic solution was washed sequentially with water, 5% aqueous sodium bicarbonate solution, water and saturated aqueous sodium chloride solution, dried (anhydrous magnesium sulfate) and evaporated to give 4-benzyl-5-(3-ethoxycarbonyl-2-hydroxy-propyl)-2,2-dimethyl-oxazolidine-3-carboxylic acid tert-butyl ester (10.11 g, 100%). Mass spectrum 422 [M+H]$^+$.

4-Benzyl-5-(3-ethoxycarbonyl-2-methanesulfonyloxy-propyl)-2,2-dimethyl-oxazolidine-3-carboxylic Acid tert-Butyl Ester

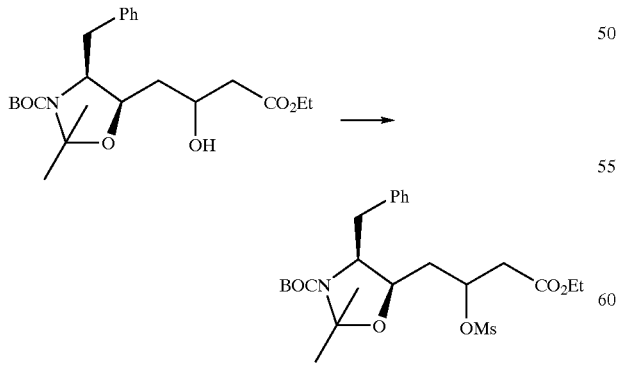

A solution of 4-benzyl-5-(3-ethoxycarbonyl-2-hydroxy-propyl)-2,2-dimethyl-oxazolidine-3-carboxylic acid tert-butyl ester (50.68 g) in pyridine (380 ml) was stirred at 15° C. under an atmosphere of nitrogen during the dropwise addition of methanesulfonyl chloride (18.4 ml). The reaction mixture was then allowed to warm to ambient temperature and stirred for a further 2 hours and evaporated. The residue was dissolved in diethyl ether, washed sequentially with 2M aqueous hydrochloric acid (500 ml and 250 ml), water, 5% aqueous sodium bicarbonate solution, water and saturated aqueous sodium chloride solution, dried (anhydrous magnesium sulfate) and evaporated to afford 4-benzyl-5-(3-ethoxycarbonyl-2-methanesulfonyloxy-propyl)-2,2-dimethyl-oxazolidine-3-carboxylic acid tert-butyl ester (64 g) as a pale yellow gum Mass spectrum 500 [M+H]$^+$.

4-Benzyl-5-(3-ethoxycarbonyl-allyl)-2,2-dimethyl-oxazolidine-3-carboxylic Acid tert-Butyl Ester

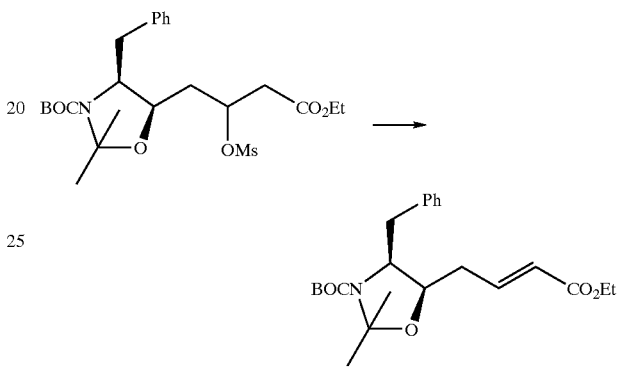

A solution of 4-benzyl-5-(3-ethoxycarbonyl-2-methanesulfonyloxy-propyl)-2,2-dimethyl-oxazolidine-3-carboxylic acid tert-butyl ester (64 g) in dichloromethane (250 ml) was stirred at 15° C. under an atmosphere of nitrogen during the dropwise addition of 1,8-diazobicyclo [5,4,0]undec-7-ene (21.3ml). After 30 minutes, a further portion of 1,8-diazobicyclo[5,4,0]undec-7-ene (9.0ml) was added and the reaction mixture stirred for 1 hour. The solvent was evaporated and the residue dissolved in ethyl acetate, washed sequentially with 2M aqueous hydrochloric acid (500 ml and 250 ml), water, 5% aqueous sodium bicarbonate solution, water and saturated aqueous sodium chloride solution, dried (anhydrous magnesium sulfate) and evaporated to afford 4-benzyl-5-(3-ethoxycarbonyl-allyl)-2, 2-dimethyl-oxazolidine-3-carboxylic acid tert-butyl ester (49 g, %) as an orange gum. Mass spectrum 404 [M+H]$^+$.

Scheme H

[2-(4-Benzyl-2-oxo-oxazolidin-3-yl)-2-oxo-ethyl] phosphoric Acid Diethyl Ester

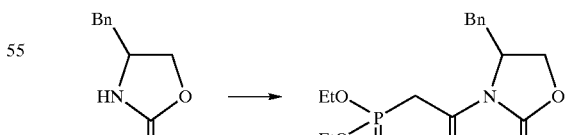

A solution of 4-benzyl-2-oxazolidinone in dry THF (300 ml) was stirred at −78° C. under nitrogen during the dropwise addition of 1.6 M n-butyl lithium in hexanes, (60 ml, 97 mmol) followed by bromo-acetyl bromide. The pale yellow solution was stirred for a further 10 minutes at −78° C. and allowed to warm to room temperature over 30 minutes. The reaction was then quenched by the addition of saturated aqueous ammonium chloride solution. After dilution with ethyl acetate and brine, the two layers were separated and the aqueous layer was extracted with ethyl acetate. The combined organic layers were washed with brine, dried (anhydrous magnesium sulfate) and concentrated in vacuo to give 4-benzyl-3-(2-bromo-acetyl)-oxazolidin-2-one (26.2 g) which was used in the next step without further purification.

A solution of 4-benzyl-3-(2-bromo-acetyl)-oxazolidin-2-one (26.2 g) in dry toluene (300 ml) was treated with triethylphosphite (17.4 ml, 101 mmol). The resulting mixture was refluxed for two hours, cooled to room temperature and concentrated in vacuo. Purification by flash chromatography on silica gel (dichloromethane/methanol: 98/2 to 95/5) provided [2-(4-benzyl-2-oxo-oxazolidin-3-yl)-2-oxo-ethyl]-phosphoric acid diethyl ester (22.27 g, 82%) as a pale yellow oil.

4-Benzyl-5-[4-(4-benzyl-2-oxo-oxazolidin-3-yl)-4-oxo-but-2-enyl]-2,2-dimethyl-oxazolidine-3-carboxylic Acid tert-Butyl Ester

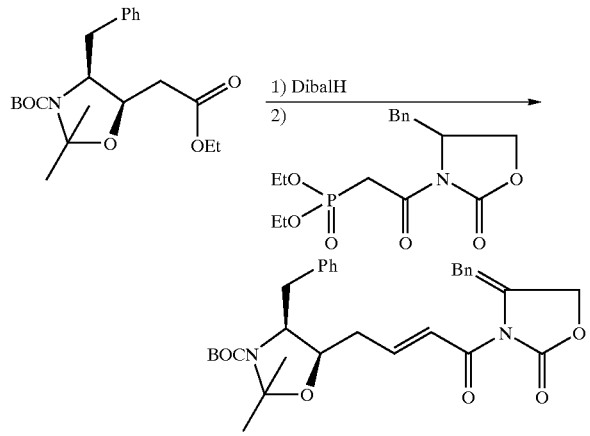

A solution of 4-benzyl-5-ethoxycarbonylmethyl-2,2-dimethyl-oxazolidine-3-carboxylic acid tert-butyl ester (30 g, 80 mol) in dry toluene (500 ml) was stirred at −78° C. during the addition of of 1M diisobutyl aluminium hydride in toluene (105 ml, 105 mmol). The resulting mixture was stirred at −78° C. for 4 hours and then ethyl acetate (60 ml) was added. After 30 minutes, the resulting mixture was allowed to warm to room temperature and a solution of potassium sodium L-tartrate tetrahydrate (90 g, mmol) in water (350 ml) was added. The resulting biphasic mixture was stirred until the two phases were clear. The layers were separated and the aqueous layer was extracted with ethyl acetate. The combined organic layers were dried (anhydrous magnesium sulfate) and concentrated in vacuo to provide 4-benzyl-2,2-dimethyl-(2-oxo-ethyl)-oxazolidine-3-carboxylic acid tert-butyl ester which solidified upon standing overnight.

A solution of [2-(4-benzyl-2-oxo-oxazolidin-3-yl)-2-oxo-ethyl]-phosphonic acid diethyl ester (36.72 g) in dry acetonitrile (550 ml) was stirred at room temperature under nitrogen and treated with lithium chloride (4.39 g) followed by the dropwise addition of 1.8-diazabicyclo (5.4.0) undec-7-ene (g, mmol). After 5 minutes, the crude 4-benzyl-2,2-dimethyl-(2-oxo-ethyl)-oxazolidine-3-carboxylic acid tert-butyl ester dissolved in dry acetonitrile (350 ml) was added via a cannula, and the resulting mixture was stirred at room temperature for 80 minutes. The mixture was then diluted with diethyl ether (1 L) and washed with brine (500 ml). The organic layer was dried (anhydrous magnesium sulfate) and concentrated in vacuo . Purification by flash chromatography on silica gel (ethyl acetate/hexane: 1/4 to 3/7) provided of 4-benzyl-5-[4-(4-benzyl-2-oxo-oxazolidin-3-yl)-4-oxo-but-2-enyl]-2,2-dimethyl-oxazolidine-3-carboxylic acid tert-butyl ester (29.33 g, 69%).

Scheme I 2-tert-Butoxycarbonylamino-3-(toluene-4-sulfonyloxy)-propionic Acid Methyl Ester

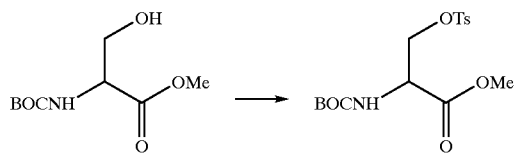

A solution of Boc-D-serine methyl ester (9.59 g, 43.8 mmol) in dichloromethane (100 ml) was stirred at −10° C. during the addition of 4-(dimethylamino)pyridine (270 mg, 2.19 mmol), triethylamine hydrochloride (4.19 g, 43.8 mmol) and tosyl chloride (8.35 g, 43.8 mmol). Triethylamine (6.10 ml, 43.8 mmol) was added dropwise at −10° C. over 35 minutes and the resultant slurry was allowed to stand at 6° C. overnight. The reaction mixture was poured into a mixture of ice (35 g), water (35 ml) and 2N hydrochloric acid (20 ml). The aqueous phase was extracted with dichloromethane (35 ml) and the combined organic solutions washed with brine (2*25 ml), dried (anhydrous magnesium sulfate) and concentrated in vacuo to a pale yellow oil. The oil was dissolved in diethyl ether (100 ml) and cooled to 6° C. Once crystallisation started, petrol ether (75 ml) was added in five portions over two hours, and crystallisation was allowed to proceed at 6° C. overnight to give 2-tert-butoxycarbonylamino-3-(toluene-4-sulfonyloxy)-propionic acid methyl ester (10.98 g, 67%).

2-tert-Butoxycarbonylamino-3-(4-fluoro-phenylsulfanyl)-propionic Acid Methyl Ester

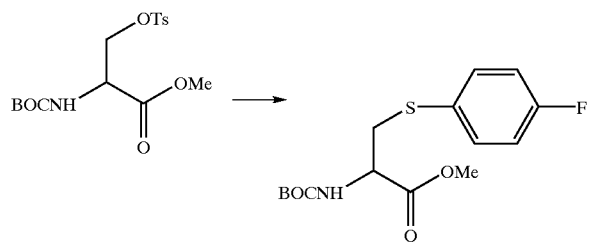

A stirred solution of 4-fluorothiophenol (1.24 g, 9.65 mmol) in N,N-dimethyl formamide (10 ml) was treated with sodium hydride (240 mg, 9.37 mmol) and the reaction mixture was stirred at room temperature for 30 minutes. 2-tert-Butoxycarbonylamino-3-(toluene-4-sulfonyloxy)-propionic acid methyl ester (3 g, 8.04 mmol) in N,N dimethyl formamide (ml) was added, the resulting mixture was stirred for two hours and then concentrated in vacuo. The residue was dissolved in ethyl acetate (100 ml) and washed with water (2*80 ml) and brine. The organic layer was dried (anhydrous magnesium sulfate) and concentrated in vacuo to give, after purification by flash chromatography on silica gel, 2-tert-butoxycarbonylamino-3-(4-fluoro-phenylsulfanyl)-propionic acid methyl ester (2.28 g, 83%) as a yellow oil.

2-tert-Butoxycarbonylamino-3-(4-fluoro-phenylsulfanyl)-propionic Acid

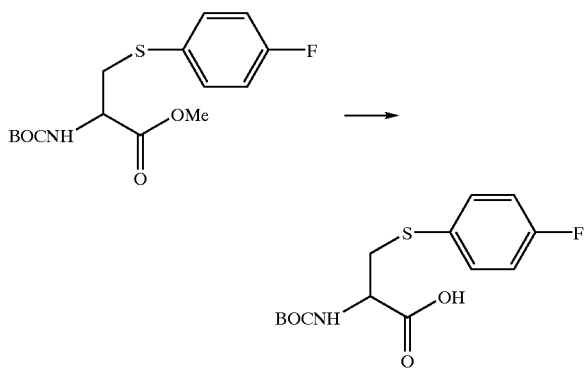

A suspension of 2-tert-butoxycarbonylamino-3-(4-fluorophenylsulfanyl)-propionic acid methyl ester (2.28 g, 6.93 mmol) in methanol (10 ml) was vigorously stirred at room temperature during the addition of 2N aqueous sodium hydroxide solution (7 ml, 14 mmol). The resulting mixture was stirred at room temperature for 2 hours and then concentrated in vacuo. The residue was diluted with water (65 ml) and the aqueous layer was extracted with diethyl ether (2*50 ml). The aqueous layer was acidified with 1N hydrochloric acid and extracted with ethyl acetate. The organic phase was dried (anhydrous magnesium sulfate) and concentrated in vacuo to give, after purification by flash chromatography on silica gel, (dichloromethane/methanol: 98/2 to 96/4) 2-tert-butoxycarbonylamino-3-(4-fluorophenylsulfanyl)-propionic acid (2.06 g, 95%) as a pale yellow oil. Mass spectrum, 315 $[M+H]^+$.

The following acids were prepared in an analogous manner:

| Name | structure | $[M + H]^+$ |
|---|---|---|
| 2-tert-Butoxycarbonylamino-3-(naphthalen-1-ylsulfanyl)-propionic acid | 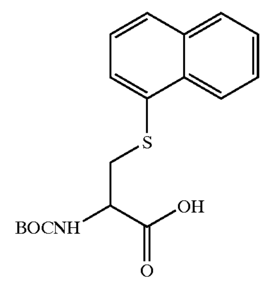 | 348 |
| 2-tert-Butoxycarbonylamino-3-(naphthalen-2-ylsulfanyl)-propionic acid | 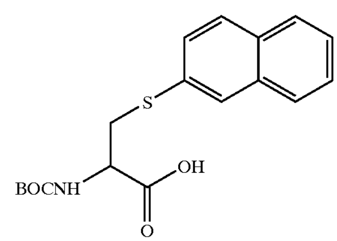 | 348 |
| 2-tert-Butoxycarbonylamino-3-(quinolin-8-ylsulfanyl)-propionic acid | 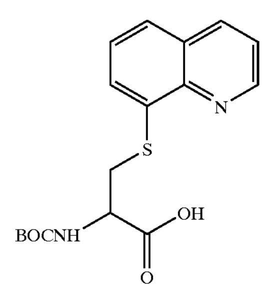 | 349 |

| Name | structure | [M + H]⁺ |
|---|---|---|
| 2-tert-Butoxycarbonylamino-3-(quinolin-2-ylsulfanyl)-propionic acid | 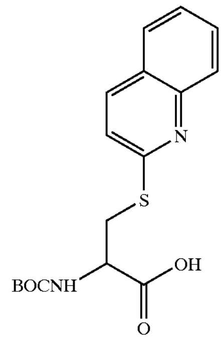 | 349 |

We claim:

1. A compound having the following formula I as individual isomers, racemates, non-racemic mixtures or mixtures of diastereoisomers;
wherein
n is 0, 1 or 2;
R$^1$ is naphthyl, quinolinyl or phenyl, optionally substituted by halogen;
R$^4$ is (C$_1$–C$_7$)-alkyl;
A is a group

A1 or

A2 wherein
R$^2$ is hydrogen or (C$_1$–C$_7$) lower alkoxy; and
R$^3$ is (C$_1$–C$_7$)-alkyl;
or pharmaceutically acceptable salts thereof.

2. A compound according to claim 1 wherein
n is 1 or 2;
R$^1$ is naphthyl, quinolinyl or phenyl;
R$^4$ is methyl; and
A is a group A1 or A2 wherein
R$^2$ is hydrogen or methoxy; and
R$^3$ is (C$_1$–C$_4$)-alkyl.

3. A compound according to claim 1 wherein
n is 1 or 2;
R$^1$ is naphthyl;
R$^4$ is methyl; and
A is a group A1 or A2 wherein
R$^2$ is hydrogen or methoxy; and
R$^3$ is (C$_1$–C$_4$)-alkyl.

4. A compound according to claim 1 wherein
n is 2;
R$^1$ is naphthyl;
R$^4$ is methyl; and
A is a group A1 or A2 wherein
R$^2$ is methoxy; and
R$^3$ is methyl.

5. A compound according to claim 1, wherein said compound is selected from the group consisting of
2-{2-Hydroxy-3-[2-methanesulfonylamino-3-(naphthalen-2-ylsulfanyl)-propionylamino]-4-phenyl-butyl}-4-methyl-cyclopentanecarboxylic acid tert-butylamide;
2-{2-Hydroxy-3-[2-methanesulfonylamino-3-(quinolin-8-ylsulfanyl)-propionylamino]-4-phenyl-butyl}-4-methyl-cyclopentanecarboxylic acid tert-butylamide;
2-{2-Hydroxy-3-[2-methanesulfonylamino-3-(naphthalen-2-ylsulfanyl)-propionylamino]-4-phenyl-butyl}-4-methyl-cyclopentanecarboxylic acid tert-butylamide;
2-{3-[3-(4-Fluoro-phenylsulfanyl)-2-methanesulfonylamino-propionylamino]-2-hydroxy-4-phenyl-butyl}-4-methyl-cyclopentanecarboxylic acid tert-butylamide;
2-{3-[3-(4-Fluoro-phenylsulfanyl)-2-methanesulfonylamino-propionylamino]-2-hydroxy-4-phenyl-butyl}-4-methyl-cyclopentanecarboxylic acid tert-butylamide;
2-2-Hydroxy-3-[2-methanesulfonylamino-3-(naphthalene-2-sulfinyl)-propionylamino]-4-phenyl-butyl}-4-methyl-cyclopentanecarboxylic acid tert-butylamide;

2-{2-Hydroxy-3-[2-methanesulfonylamino-3-(naphthalene-2-sulfonyl)-propionylamino]-4-phenyl-butyl}-4-methyl-cyclopentanecarboxylic acid tert-butylamide;

2-{2-Hydroxy-3-[2-methanesulfonylamino-3-(naphthalene-2-sulfonyl)-propionylamino]-4-phenyl-butyl}-4-methyl-cyclopentanecarboxylic acid tert-butylamide;

2-{2-Hydroxy-3-[2-methanesulfonylamino-3-(quinoline-8-sulfonyl)-propionylamino]-4-phenyl-butyl}-4-methyl-cyclopentanecarboxylic acid tert-butylamide; and 2-{3-[3-(4-Fluoro-benzenesulfonyl)-2-methanesulfonylamino-propionylamino]-2-hydroxy-4-phenyl-butyl}-4-methyl-cyclopentanecarboxylic acid tert-butylamide.

6. A compound according to claim 1, wherein said compound is selected from the group consisting of 2-{2-Hydroxy-3-[2-methanesulfonylamino-3-(naphthalen-1-ylsulfanyl)-propionylamino]-4-phenyl-butyl}-4-methoxy-cyclohexanecarboxylic acid tert-butylamide;

N-tert-Butyl-2-[2-hydroxy-3-[[N2-(methanesulfonyl)-S-(2-naphthyl)-D-cysteinyl]amino]-4-phenylbutyl]-4-methoxy-1-cyclohexanecarboxamide;

2-{3-[3-(4-Fluoro-phenylsulfanyl)-2-methanesulfonylamino-propionylamino]-2-hydroxy-4-phenyl-butyl}-4-methoxy-cyclohexanecarboxylic acid tert-butylamide;

2-{2-Hydroxy-3-[2-methanesulfonylamino-3-(naphthalen-1-ylsulfanyl)-propionylamino]-4-phenyl-butyl}-5-methoxy-cyclohexanecarboxylic acid tert-butylamide;

2-{2-Hydroxy-3-[2-methanesulfonylamino-3-(naphthalen-2-ylsulfanyl)-propionylamino]-4-phenyl-butyl}-5-methoxy-cyclohexanecarboxylic acid tert-butylamide;

2-{2-Hydroxy-3-[2-methanesulfonylamino-3-(quinolin-8-ylsulfanyl)-propionylamino]-4-phenyl-butyl}-5-methoxy-cyclohexanecarboxylic acid tert-butylamide;

2-{3-[3-(4-Fluoro-phenylsulfanyl)-2-methanesulfonylamino-propionylamino]-2-hydroxy-4-phenyl-butyl}-5-methoxy-cyclohexanecarboxylic acid tert-butylamide;

2-{2-Hydroxy-3-[2-methanesulfonylamino-3-(naphthalen-1-ylsulfanyl)-propionylamino]-4-phenyl-butyl}-cyclohexanecarboxylic acid tert-butylamide;

2-{2-Hydroxy-3-[2-methanesulfonylamino-3-(naphthalen-1-ylsulfinyl)-propionylamino]-4-phenyl-butyl}-4-methoxy-cyclohexanecarboxylic acid tert-butylamide;

2-{2-Hydroxy-3-[2-methanesulfonylamino-3-(naphthalene-2-sulfinyl)-propionylamino]-4-phenyl-butyl}-4-methoxy-cyclohexanecarboxylic acid tert-butylamide;

2-{3-[3-(4-Fluoro-benzenesulfinyl)-2-methanesulfonylamino-propionylamino]-2-hydroxy-4-phenyl-butyl}-4-methoxy-cyclohexanecarboxylic acid tert-butylamide;

2-{2-Hydroxy-3-[2-methanesulfonylamino-3-(naphthalene-1-sulfinyl)-propionylamino]-4-phenyl-butyl}-5-methoxy-cyclohexanecarboxylic acid tert-butylamide;

2-{2-Hydroxy-3-[2-methanesulfonylamino-3-(naphthalene-2-sulfinyl)-propionylamino]-4-phenyl-butyl}-5-methoxy-cyclohexanecarboxylic acid tert-butylamide;

2-{2-Hydroxy-3-[2-methanesulfonylamino-3-(naphthalene-1-sulfinyl)-propionylamino]-4-phenyl-butyl}-cyclohexanecarboxylic acid tert-butylamide;

2-{2-Hydroxy-3-[2-methanesulfonylamino-3-(naphthalene-1-sulfonyl)-propionylamino]-4-phenyl-butyl}-4-methoxy-cyclohexanecarboxylic acid tert-butylamide;

N-tert-Butyl-2-[2-hydroxy-3-[[N2-(methanesulfonyl)-S-(2-naphthyl)-D-cysteinyl]amino]-4-phenylbutyl]-4-methoxy-1-cyclohexanecarboxamide S,S-dioxide;

2-{3-[-(4-Fluoro-benzenesulfonyl)-2-methanesulfonylamino-propionylamino]-2-hydroxy-4-phenyl-butyl}-4-methoxy-cyclohexanecarboxylic acid tert-butylamide;

2-{2-Hydroxy-3-[2-methanesulfonylamino-3-(naphthalene-1-sulfonyl)-propionylamino]-4-phenyl-butyl}-5-methoxy-cyclohexanecarboxylic acid tert-butylamide;

2-{2-Hydroxy-3-[2-methanesulfonylamino-3-(naphthalene-2-sulfonyl)-propionylamino]-4-phenyl-butyl}-5-methoxy-cyclohexanecarboxylic acid tert-butylamide;

2-{2-Hydroxy-3-[2-methanesulfonylamino-3-(quinoline-8-sulfonyl)-propionylamino]-4-phenyl-butyl}-5-methoxy-cyclohexanecarboxylic acid tert-butylamide;

2-{3-[3-(4-Fluoro-benzenesulfonyl)-2-methanesulfonylamino-propionylamino]-2-hydroxy-4-phenyl-butyl}-5-methoxy-cyclohexanecarboxylic acid tert-butylamide;

2-{2-Hydroxy-3-[2-methanesulfonylamino-3-(naphthalene-1-sulfonyl)-propionylamino]-4-phenyl-butyl}-cyclohexanecarboxylic acid tert-butylamide;

2-{2-Hydroxy-3-[2-methanesulfonylamino-3-(quinoline-8-sulfonyl)-propionylamino]-4-phenyl-butyl}-4-methoxy-cyclohexanecarboxylic acid tert-butylamide; and 2-{2-Hydroxy-3-[2-methanesulfonylamino-3-(quinoline-2-sulfonyl)-propionylamino]-4-phenyl-butyl}-4-methoxy-cyclohexanecarboxylic acid tert-butylamide.

7. A method of treating or preventing a disease mediated by the human immunodeficiency virus (HIV) comprising administering to a patient in need of such treatment, an effective amount of a compound of the following formula I

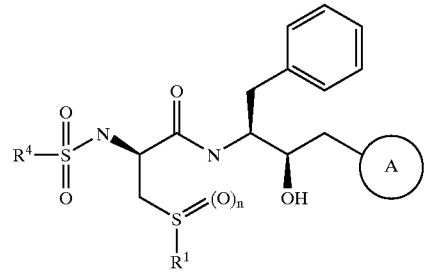

as individual isomers, racemates, non-racemic mixtures or mixtures of diastereoisomers;

wherein n is 0, 1 or 2;

$R^1$ is naphthyl, quinolinyl or phenyl, optionally substituted by halogen;

$R^4$ is $(C_1-C_7)$-alkyl;

A is a group

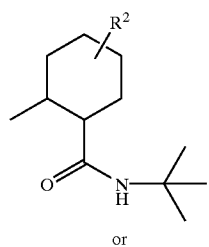
A1 or

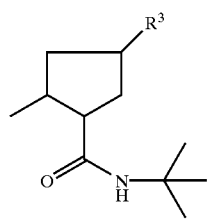
A2 wherein
R² is hydrogen or (C₁–C₇) lower alkoxy; and
R³ is (C₁–C₇)-alkyl;
or pharmaceutically acceptable salts thereof.

8. A pharmaceutical composition comprising a pharmaceutically effective amount of a compound of the following formula I

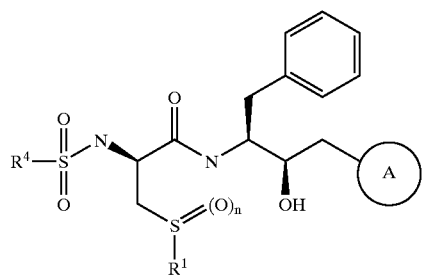
I as individual isomers, racemates, non-racemic mixtures or mixtures of diastereoisomers;

wherein n is 0, 1 or 2;
R¹ is naphthyl, quinolinyl or phenyl, optionally substituted by halogen;
R⁴ is (C₁–C₇)-alkyl;
A is a group

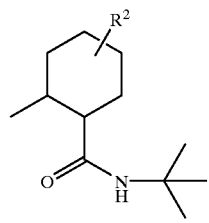
A1 or

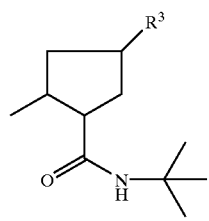
A2 wherein
R² is hydrogen or (C₁–C₇) lower alkoxy; and
R³ is (C₁–C₇)-alkyl;

or pharmaceutically acceptable salts thereof.

* * * * *